US008691758B2

(12) United States Patent
Britt et al.

(10) Patent No.: US 8,691,758 B2
(45) Date of Patent: *Apr. 8, 2014

(54) INHIBITORS OF SERINE PROTEASES, PARTICULARLY HCV NS3-NS4A PROTEASE

(75) Inventors: Shawn D. Britt, Andover, MA (US); Kevin M. Cottrell, Cambridge, MA (US); Robert B. Perni, Marlborough, MA (US); Janos Pitlik, Westborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 214 days.

This patent is subject to a terminal disclaimer.

(21) Appl. No.: 11/434,008

(22) Filed: May 15, 2006

(65) Prior Publication Data
US 2006/0211629 A1  Sep. 21, 2006

Related U.S. Application Data

(63) Continuation of application No. 10/893,748, filed on Jul. 16, 2004, now Pat. No. 7,109,172.

(60) Provisional application No. 60/488,535, filed on Jul. 18, 2003.

(51) Int. Cl.
*A61K 38/00* (2006.01)
*A01N 37/18* (2006.01)

(52) U.S. Cl.
USPC .......................................... 514/4.3

(58) Field of Classification Search
None
See application file for complete search history.

(56) References Cited

U.S. PATENT DOCUMENTS

| | | | |
|---|---|---|---|
| 6,265,380 B1 | 7/2001 | Tung et al. | 514/17 |
| 6,608,067 B1 | 8/2003 | Tung et al. | |
| 6,617,309 B2 | 9/2003 | Tung et al. | |
| 6,800,434 B2 * | 10/2004 | Saksena et al. | 435/5 |
| 6,909,000 B2 | 6/2005 | Farmer et al. | 544/406 |
| 7,109,172 B2 | 9/2006 | Britt et al. | |
| 7,208,600 B2 | 4/2007 | Cottrell et al. | |
| 7,241,796 B2 | 7/2007 | Farmer et al. | |
| 7,273,885 B2 | 9/2007 | Pitlik et al. | |
| 7,365,092 B2 | 4/2008 | Cottrell et al. | |
| 7,378,422 B2 | 5/2008 | Perni et al. | |
| 2003/0236242 A1 | 12/2003 | Perni et al. | |
| 2004/0077600 A1 | 4/2004 | Tung et al. | 514/64 |
| 2004/0266731 A1 | 12/2004 | Tung et al. | 514/79 |
| 2005/0090450 A1 | 4/2005 | Farmer et al. | |
| 2005/0119189 A1 | 6/2005 | Cottrell et al. | |
| 2005/0137139 A1 | 6/2005 | Perni et al. | |
| 2005/0197299 A1 | 9/2005 | Babine et al. | |
| 2005/0215486 A1 | 9/2005 | Cottrell et al. | |
| 2006/0211629 A1 | 9/2006 | Britt et al. | |
| 2007/0161789 A1 | 7/2007 | Cottrell et al. | |
| 2007/0179167 A1 | 8/2007 | Cottrell et al. | |
| 2007/0292933 A1 | 12/2007 | Pitlik et al. | |
| 2008/0045480 A1 | 2/2008 | Farmer et al. | |
| 2008/0125376 A1 | 5/2008 | Cottrell et al. | |
| 2008/0311079 A1 | 12/2008 | Perni et al. | |
| 2009/0022688 A1 | 1/2009 | Farmer et al. | |

FOREIGN PATENT DOCUMENTS

| | | |
|---|---|---|
| WO | WO 98/17679 A1 | 4/1998 |
| WO | WO 01/74768 A2 | 11/2001 |
| WO | WO 02/08244 A2 | 1/2002 |
| WO | WO 02/08256 A2 | 1/2002 |
| WO | WO 02/18369 A2 | 3/2002 |
| WO | WO 03/006490 A1 | 1/2003 |
| WO | WO 03/035060 A1 | 5/2003 |
| WO | WO 03/087092 A2 | 10/2003 |
| WO | WO 2004/022161 A1 | 10/2004 |
| WO | WO 2004/092161 A1 | 10/2004 |
| WO | WO 2005/028502 A1 | 3/2005 |
| WO | WO 2005/035525 A2 | 4/2005 |
| WO | WO 2005/037860 A2 | 4/2005 |
| WO | WO 2005/077969 A2 | 8/2005 |
| WO | 2008106058 | 9/2008 |

\* cited by examiner

*Primary Examiner* — Thomas Heard
(74) *Attorney, Agent, or Firm* — Lisa A. Dixon; Susan C. Kelly

(57) ABSTRACT

The present invention relates to compounds of formula I or formula Ia or pharmaceutically acceptable salts thereof, that inhibit serine protease activity, particularly the activity of hepatitis C virus NS3-NS4A protease. As such, they act by interfering with the life cycle of the hepatitis C virus and are useful as antiviral agents. The invention further relates to pharmaceutically acceptable compositions comprising said compounds either for ex vivo use or for administration to a patient suffering from HCV infection and processes for preparing the compounds. The invention also relates to methods of treating an HCV infection in a patient by administering a pharmaceutical composition comprising a compound of this invention.

1 Claim, No Drawings

US 8,691,758 B2

INHIBITORS OF SERINE PROTEASES, PARTICULARLY HCV NS3-NS4A PROTEASE

CROSS REFERENCE TO RELATED APPLICATIONS

This application is a continuation of co-pending U.S. patent application Ser. No. 10/893,748, filed Jul. 16, 2004, entitled "Inhibitors of Serine Proteases, Particularly HCV NS3-NS4A Protease", which claims the benefit of U.S. Provisional Patent Application 60/488,535, filed Jul. 18, 2003, entitled "Inhibitors of Serine Proteases, Particularly HCV NS3-NS4A Protease", both of which are incorporated in their entirety herein by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to pharmaceutical compositions comprising these compounds either for ex vivo use or for administration to a patient suffering from HCV infection. The invention also relates to processes for preparing the compounds and methods of treating an HCV infection in a patient by administering a pharmaceutical composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.,* 23, pp. 437-455 (1994); M. J. Alter "Hepatitis C Virus Infection in the United States," *J. Hepatology,* 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews,* 14, pp. 201-204 (1994); D. Lavanchy, "Global Surveillance and Control of Hepatitis C," *J. Viral Hepatitis,* 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews,* 14, pp. 211-220 (1994); I. Saito et. al., "Hepatitis C Virus Infection is Associated with the Development of Hepatocellular Carcinoma," *Proc. Natl. Acad. Sci. USA,* 87, pp. 6547-6549 (1990)]. Unfortunately, there are no broadly effective treatments for the debilitating progression of chronic HCV.

HCV is a RNA virus of the Flaviviridae family. Acute infection with HCV causes a generally mild, often asymptomatic, acute hepatitis. However, at least 85% of patients infected with HCV do not fully clear the virus and develop chronic infection of the liver. Once chronic hepatitis C is established, spontaneous clearance of the virus is rare and the majority of patients with chronic hepatitis C develop slowly progressive liver disease. Twenty years after infection, most patients have evidence of ongoing chronic hepatitis and at least 20% have cirrhosis. Long-term sequelae of chronic hepatitis C include cirrhosis, hepatic failure, and hepatocellular carcinoma. It is estimated that HCV infects 170 million persons worldwide. Over the next ten years, as a larger proportion of patients who are currently infected enter the third decade of their infection, the number of deaths attributed to hepatitis C is expected to significantly increase.

Typical symptoms of HCV infection include elevated ALT, positive test for anti-HCV antibodies, presence of HCV as demonstrated by a positive test for HCV-RNA, clinical stigmata of chronic liver disease, or hepatocellular damage.

The HCV genome encodes a polyprotein of 3010-3033 amino acids [Q. L. Choo, et. al., "Genetic Organization and Diversity of the Hepatitis C Virus." *Proc. Natl. Acad. Sci. USA,* 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA,* 87, pp. 9524-9528 (1990); A. Takamizawa et. al., "Structure and Organization of the Hepatitis C Virus Genome Isolated From Human Carriers," *J. Virol.,* 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.,* 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.,* 67, pp. 2832-2843 (1993); A. Grakoui et. al., "Expression and Identification of Hepatitis C Virus Polyprotein Cleavage Products," *J. Virol.,* 67, pp. 1385-1395 (1993); L. Tomei et. al., "NS3 is a serine protease required for processing of hepatitis C virus polyprotein", *J. Virol.,* 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA,* 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.,* 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man, indicating that interrupting this stage of the viral life cycle results in therapeutically active agents. Consequently HCV NS3 serine protease is also an attractive target for drug discovery.

Furthermore, the current understanding of HCV has not led to any other satisfactory anti-HCV agents or treatments. Until recently, the only established therapy for HCV disease was interferon treatment (see, e.g., PCT publication No. WO 02/18369, the disclosure of which is herein incorporated by reference). However, interferons have significant side effects [M. A. Wlaker et al., "Hepatitis C Virus: An Overview of Current Approaches and Progress," *DDT,* 4, pp. 518-29 (1999); D. Moradpour et al., "Current and Evolving Therapies for Hepatitis C," *Eur. J. Gastroenterol. Hepatol.,* 11, pp. 1199-1202 (1999); H. L. A. Janssen et al. "Suicide Associated with Alfa-Interferon Therapy for Chronic Viral Hepatitis," *J. Hepatol.,* 21, pp. 241-243 (1994); P. F. Renault et al., "Side Effects of Alpha Interferon," *Seminars in Liver Disease,* 9, pp. 273-277. (1989)] and induce long term remission in only a fraction (~25%) of cases [O. Weiland, "Interferon Therapy in Chronic Hepatitis C Virus Infection", *FEMS Microbiol. Rev.,* 14, pp. 279-288 (1994)]. Ribavirin, a broad spectrum antiviral agent, has reported acitivty in chronic hepatitis C. Recent introductions of the pegylated forms of interferon (PEG-Intron® and Pegasys®) and the combination therapy of ribavirin and pegylated interferon (Rebetrol®) have resulted in only modest improvements in remission rates and only partial reductions in side effects (see, e.g., U.S. Pat. No. 6,299,872, U.S. Pat. No. 6,387,365, U.S. Pat. No. 6,172,046, U.S. Pat. No. 6,472,373, the disclosures of which are incorporated herein by reference). Moreover, the prospects for effective anti-HCV vaccines remain uncertain.

Thus, there is a need for more effective anti-HCV therapies particularly compounds that may be used as protease inhibitors. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

The present invention provides compounds that are potent binders and inhibitors of the HCV NS3/NS4A serine protease and are, therefore, useful as anti-HCV agents.

SUMMARY OF THE INVENTION

The present invention provides a compound of formula I:

I or a pharmaceutically acceptable salt thereof,
wherein:
X and X' are both fluorine; or
X and X' are independently C(H), N, NH, O, or S; and X and X' are taken together with the carbon atom to which they are bound to form a 5- to 7-membered saturated or partially unsaturated ring having up to 4 heteroatoms independently selected from N, NH, O, S, SO, and $SO_2$; wherein any atom is optionally singly or multiply substituted with up to 3 substituents selected independently from J; and wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;

J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O)OR', —C(O)C(O)NR', —C(O)$CH_2$C(O) R', —C(S)R', —C(S)OR', —C(O)OR', —OC(O)R', —C(O)N(R')$_2$, —OC(O)N(R')$_2$, —C(S)N(R')$_2$, —($CH_2$)$_{0-2}$NHC(O)R', —N(R')N(R')COR', —N(R')N (R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N (R')$_2$, —N(COR')COR', —N(OR')R', —C(=NH) N(R')$_2$, —C(O)N(OR')R', —C(=NOR')R', —OP(O) (OR')$_2$, —P(O)(R')$_2$, —P(O)(OR')$_2$, or —P(O)(H) (OR'); wherein;
R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom form a 3- to 10-membered aromatic or non-aromatic ring having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;
Y and Y' are independently:
hydrogen-,
(C1-C12)-aliphatic-,
(C3-C10)-cycloalkyl- or -cycloalkenyl-,
(C3-C10)-cycloalkyl-(C1-C12)-aliphatic-,
(C6-C10)-aryl-,
(C3-C10)-heterocyclyl-; or
(C5-C10)-heteroaryl-;
wherein up to three aliphatic carbon atoms in Y and Y' may be replaced by O, N, NH, S, SO, or $SO_2$;
wherein each of Y and Y' is independently and optionally substituted with up to 3 substituents independently selected from J;
$R_1$ and $R_3$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in $R_1$ and $R_3$ may be replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;
$R_2$, $R_4$, and $R_7$ are independently:
hydrogen-,
(C1-C12)-aliphatic-,
(C3-C10)-cycloalkyl-(C1-C12)-aliphatic-, or (C6-C10)-aryl-(C1-C12)-aliphatic-;
    wherein up to two aliphatic carbon atoms in $R_2$, $R_4$, and $R_7$ may be replaced by a heteroatom selected from O, N, NH, S, SO, and $SO_2$ in a chemically stable arrangement;
    wherein each of $R_2$, $R_4$, and $R_7$ is independently and optionally substituted with up to 3 substituents independently selected from J;
$R_5$ and $R_{5'}$ are independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$, is H, wherein said Ph or —$CH_2$Ph group is optionally substituted with up to 3 substituents independently selected from J; or
$R_5$ and $R_{5'}$ together with the atom to which they are bound is a 3- to 6-membered saturated or partially unsaturated ring having up to 2 heteroatoms selected from N, NH, O, SO, and $SO_2$; wherein the ring has up to 2 substituents selected independently from J;
W is:

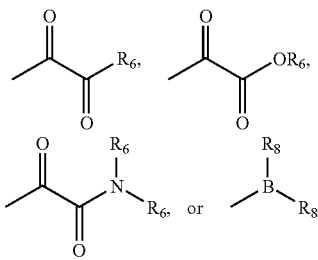

wherein each $R_6$ is independently:
    hydrogen-,
    (C1-C12)-aliphatic-,
    (C6-C10)-aryl-,
    (C6-C10)-aryl-(C1-C12)aliphatic-,
    (C3-C10)-cycloalkyl- or cycloalkenyl-,
    [(C3-C10)-cycloalkyl- or cycloalkenyl]-(C1-C12)-aliphatic-,
    (C3-C10)-heterocyclyl-,
    (C3-C10)-heterocyclyl-(C1-C12)-aliphatic-,
    (C5-C10)-heteroaryl-, or
    (C5-C10)-heteroaryl-(C1-C12)-aliphatic-, or
    two $R_6$ groups, which are bound to the same nitrogen atom, form together with that nitrogen atom, a (C3-C10)-heterocyclic ring;
    wherein $R_6$ is optionally substituted with up to 3 J substituents;
wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;
V is O or a valence bond; and
T is:
    (C1-C12)-aliphatic-;
    (C6-C10)-aryl-,
    (C6-C10)-aryl-(C1-C12)aliphatic-,
    (C3-C10)-cycloalkyl or -cycloalkenyl-,
    [(C3-C10)-cycloalkyl or -cycloalkenyl]-(C1-C12)-aliphatic-,
    (C3-C10)-heterocyclyl-,
    (C3-C10)-heterocyclyl-(C1-C12)-aliphatic-,
    (C5-C10)-heteroaryl-, or
    (C5-C10)-heteroaryl-(C1-C12)-aliphatic-;
        wherein up to 3 aliphatic carbon atoms in T may be replaced by a heteroatom selected from O, N, NH, S, SO, or $SO_2$ in a chemically stable arrangement;
        wherein each T is optionally substituted with up to 3 J substituents;
provided that the following compounds are excluded:
a) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester glycine;
b) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
c) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
d) N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
e) N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
f) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester, glycine;
g) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
h) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
i) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
j) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
k) N-acetyl-L-α-glutamyl-L-α-glutamyl-L-valyl-L-valyl-N-[1-[oxo(2-propenylamino)acetyl]butyl]-,bis(1,1-dimethylethyl)ester-(8S)-1,4-dithia-7-azaspiro[4.4]nonane-8-carboxamide;
l) N-acetyl-L-α-glutamyl-L-α-glutamyl-L-valyl-L-valyl-N-[1-[oxo(2-propenylamino)acetyl]butyl]-,2-(1,1-dimethylethyl)ester-(8S)-1,4-dithia-7-azaspiro[4.4]nonane-8-carboxamide;
m) N-acetyl-L-α-glutamyl-L-α-glutamyl-L-valyl-L-valyl-N-[1-[oxo(2-propenylamino)acetyl]butyl]-(8S)-1,4-dithia-7-azaspiro[4.4]nonane-8-carboxamide;
n) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-glycine;
o) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoylglycyl-2-phenyl-glycinamide;
p) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-,1,2-bis(1,1-dimethylethyl)-7-(2-propenyl)ester glycine; and
q) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-1,2-bis(1,1-dimethylethyl)ester glycine.

The invention also relates to processes for preparing the above compounds and to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

DETAILED DESCRIPTION OF THE INVENTION

The present invention provides a compound of formula I:

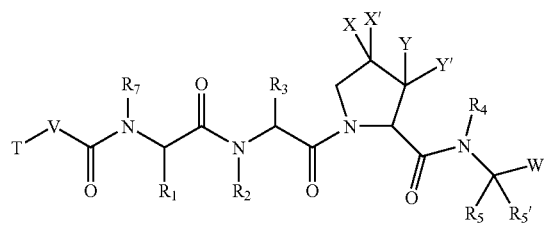

I or a pharmaceutically acceptable salt thereof,
wherein:
X and X' are both fluorine; or
X and X' are independently C(H), N, NH, O, or S; and X and X' are taken together with the carbon atom to which they are bound to form a 5- to 7-membered saturated or partially unsaturated ring having up to 4 heteroatoms independently selected from N, NH, O, S, SO, and $SO_2$; wherein any atom is optionally singly or multiply substituted with up to 3 substituents selected independently from J; and wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;

J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O)OR', —C(O)C(O)NR', —C(O)$CH_2$C(O) R', —C(S)R', —C(S)OR', —C(O)OR', —OC(O)R', —C(O)N(R')$_2$, —OC(O)N(R')$_2$, —C(S)N(R')$_2$, —($CH_2$)$_{0-2}$NHC(O)R', —N(R')N(R')COR', —N(R')N (R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N (R')$_2$, —N(COR')COR', —N(OR')R', —C(=NH) N(R')$_2$, —C(O)N(OR')R', —C(=NOR')R', —OP(O) (OR')$_2$, —P(O)(R')$_2$, —P(O)(OR')$_2$, or —P(O)(H) (OR'); wherein:
R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom form a 3- to 10-membered aromatic or non-aromatic ring having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;

Y and Y' are independently:
hydrogen-,
(C1-C12)-aliphatic-,
(C3-C10)-cycloalkyl- or -cycloalkenyl-,
(C3-C10)-cycloalkyl-(C1-C12)-aliphatic-,
(C6-C10)-aryl-,
(C3-C10)-heterocyclyl-; or
(C5-C10)-heteroaryl-;
wherein up to three aliphatic carbon atoms in Y and Y' may be replaced by O, N, NH, S, SO, or $SO_2$;
wherein each of Y and Y' is independently and optionally substituted with up to 3 substituents independently selected from J;

$R_1$ and $R_3$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in $R_1$ and $R_3$ may be replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;

$R_2$, $R_4$, and $R_7$ are independently:
hydrogen-,
(C1-C12)-aliphatic-,
(C3-C10)-cycloalkyl-(C1-C12)-aliphatic-, or
(C6-C10)-aryl-(C1-C12)-aliphatic-;
wherein up to two aliphatic carbon atoms in $R_2$, $R_4$, and $R_7$ may be replaced by a heteroatom selected from O, N, NH, S, SO, and $SO_2$ in a chemically stable arrangement;
wherein each of $R_2$, $R_4$, and $R_7$ is independently and optionally substituted with up to 3 substituents independently selected from J;

$R_5$ and $R_{5'}$ are independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or $R_5$ and $R_{5'}$ together with the atom to which they are bound is a 3- to 6-membered saturated or partially unsaturated ring having up to 2 heteroatoms selected from N, NH, O, SO, and $SO_2$; wherein the ring has up to 2 substituents selected independently from J;

W is:

$$\begin{array}{cccc}
& O & & O \\
& \parallel & & \parallel \\
CH_3-C-R_6, & & CH_3-C-OR_6, \\
& O & & \\
& \parallel & R_6 & R_8 \\
CH_3-C-N & & & \\
& \parallel & R_6, \text{ or} & B \\
& O & & R_8
\end{array}$$

wherein each $R_6$ is independently:
- hydrogen-,
- (C1-C12)-aliphatic-,
- (C6-C10)-aryl-,
- (C6-C10)-aryl-(C1-C12)aliphatic-,
- (C3-C10)-cycloalkyl- or cycloalkenyl-,
- [(C3-C10)-cycloalkyl- or cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-, or
- two $R_6$ groups, which are bound to the same nitrogen atom, form together with that nitrogen atom, a (C3-C10)-heterocyclic ring;
- wherein $R_6$ is optionally substituted with up to 3 J substituents;
- wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;

V is O or a valence bond; and

T is:
- (C1-C12)-aliphatic-;
- (C6-C10)-aryl-,
- (C6-C10)-aryl-(C1-C12)aliphatic-,
- (C3-C10)-cycloalkyl or -cycloalkenyl-,
- [(C3-C10)-cycloalkyl or -cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-;
  - wherein up to 3 aliphatic carbon atoms in T may be replaced by a heteroatom selected from O, N, NH, S, SO, or $SO_2$ in a chemically stable arrangement;
  - wherein each T is optionally substituted with up to 3 J substituents;

provided that the following compounds are excluded:
a) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester glycine;
b) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
c) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
d) N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
e) N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
f) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester, glycine;
g) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
h) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
i) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
j) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
k) N-acetyl-L-α-glutamyl-L-α-glutamyl-L-valyl-L-valyl-N-[1-[oxo(2-propenylamino)acetyl]butyl]-,bis(1,1-dimethylethyl)ester-(8S)-1,4-dithia-7-azaspiro[4.4]nonane-8-carboxamide;
l) N-acetyl-L-α-glutamyl-L-α-glutamyl-L-valyl-L-valyl-N-[1-[oxo(2-propenylamino)acetyl]butyl]-,2-(1,1-dimethylethyl)ester-(8S)-1,4-dithia-7-azaspiro[4.4]nonane-8-carboxamide;
m) N-acetyl-L-α-glutamyl-L-α-glutamyl-L-valyl-L-valyl-N-[1-[oxo(2-propenylamino)acetyl]butyl]-(8S)-1,4-dithia-7-azaspiro[4.4]nonane-8-carboxamide;
n) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-glycine;
o) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoylglycyl-2-phenyl-glycinamide;
p) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-,1,2-bis(1,1-dimethylethyl)-7-(2-propenyl)ester glycine; and
q) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-1,2-bis(1,1-dimethylethyl)ester glycine.

DEFINITIONS

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring.

The term "heterocyclyl" as used herein means a monocyclic or bicyclic non-aromatic ring system having 1 to 3 heteroatom or heteroatom groups in each ring selected from O, N, NH, S, SO, and $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a C5, C6, C7, C8, C9, and C10 monocyclic or bicyclic non-aromatic ring system having 1 to 3 heteroatom or heteroatom groups in each ring selected from O, N, NH, and S in a chemically stable arrangement.

The term "heteroaryl" as used herein means a monocyclic or bicyclic aromatic ring system having 1 to 3 heteroatom or heteroatom groups in each ring selected from O, N, NH, and S in a chemically stable arrangement. In such a bicyclic aromatic ring system embodiment of "heteroaryl":

one or both rings may be aromatic; and one or both rings may contain said heteroatom or heteroatom groups. It is understood that as used herein, the term "(C5-C10)-heteroaryl-" includes any one of a C5, C6, C7, C8, C9, and C10 monocyclic or bicyclic aromatic ring system having 1 to 3 heteroatom or heteroatom groups in each ring selected from O, N, NH, and S in a chemically stable arrangement.

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is also understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Examples of cycloalkyl groups include cyclopropyl, cyclobutyl, cyclopentyl, cyclohexyl, cyclohexenyl, cycloheptyl, cycloheptenyl, nornbornyl, adamantyl and decalin-yl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

EMBODIMENTS

According to one embodiment, the compounds of the present invention are of formula I:

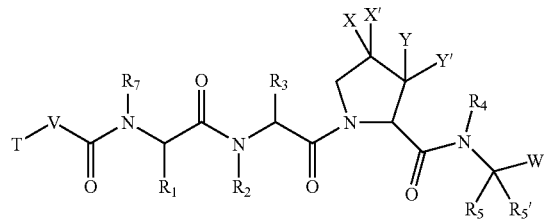

or a pharmaceutically acceptable salt thereof,
wherein:
X and X' are both fluorine; or
X and X' are independently C(H), N, NH, O, or S; and X and X' are taken together with the carbon atom to which they are bound to form a 5- to 7-membered saturated or partially unsaturated ring having up to 4 heteroatoms independently selected from N, NH, O, S, SO, and $SO_2$; wherein any atom is optionally singly or multiply substituted with up to 3 substituents selected independently from J; and wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;

J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O)OR', —C(O)C(O)NR', —C(O)$CH_2$C(O)R', —C(S)R', —C(S)OR', —C(O)OR', —OC(O)R', —C(O)N(R')$_2$, —OC(O)N(R')$_2$, —C(S)N(R')$_2$, —($CH_2$)$_{0-2}$NHC(O)R', —N(R')N(R')COR', —N(R')N(R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); wherein;

R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom form a 3- to 10-membered aromatic or non-aromatic ring having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;

Y and Y' are independently:
hydrogen-,
(C1-C12)-aliphatic-,
(C3-C10)-cycloalkyl- or -cycloalkenyl-,
(C3-C10)-cycloalkyl-(C1-C12)-aliphatic-,
(C6-C10)-aryl-,
(C3-C10)-heterocyclyl-; or
(C5-C10)-heteroaryl-;
wherein up to three aliphatic carbon atoms in Y and Y' may be replaced by O, N, NH, S, SO, or $SO_2$;
wherein each of Y and Y' is independently and optionally substituted with up to 3 substituents independently selected from J;

$R_1$ and $R_3$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in $R_1$ and $R_3$ may be replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;

$R_2$, $R_4$, and $R_7$ are independently:
  hydrogen-,
  (C1-C12)-aliphatic-,
  (C3-C10)-cycloalkyl-(C1-C12)-aliphatic-, or
  (C6-C10)-aryl-(C1-C12)-aliphatic-;
    wherein up to two aliphatic carbon atoms in $R_2$, $R_4$, and $R_7$ may be replaced by a heteroatom selected from O, N, NH, S, SO, and $SO_2$ in a chemically stable arrangement;
    wherein each of $R_2$, $R_4$, and $R_7$ is independently and optionally substituted with up to 3 substituents independently selected from J;
$R_5$ and $R_{5'}$ are independently hydrogen or (C1-C12)-aliphatic, wherein any hydrogen is optionally replaced with halogen; wherein any terminal carbon atom of $R_5$ is optionally substituted with sulfhydryl or hydroxy; or $R_5$ is Ph or —$CH_2$Ph and $R_{5'}$ is H, wherein said Ph or —$CH_2$Ph group is optionally substituted with up to 3 substituents independently selected from J; or
$R_5$ and $R_{5'}$ together with the atom to which they are bound is a 3- to 6-membered saturated or partially unsaturated ring having up to 2 heteroatoms selected from N, NH, O, SO, and $SO_2$; wherein the ring has up to 2 substituents selected independently from J;
W is:

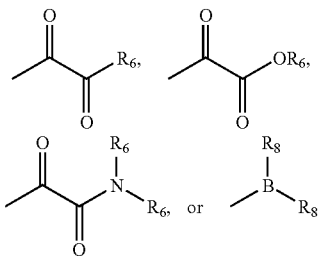

wherein each $R_6$ is independently:
    hydrogen-,
    (C1-C12)-aliphatic-,
    (C6-C10)-aryl-,
    (C6-C10)-aryl-(C1-C12)aliphatic-,
    (C3-C10)-cycloalkyl- or cycloalkenyl-,
    [(C3-C10)-cycloalkyl- or cycloalkenyl]-(C1-C12)-aliphatic-,
    (C3-C10)-heterocyclyl-,
    (C3-C10)-heterocyclyl-(C1-C12)-aliphatic-,
    (C5-C10)-heteroaryl-, or
    (C5-C10)-heteroaryl-(C1-C12)-aliphatic-, or
    two $R_6$ groups, which are bound to the same nitrogen atom, form together with that nitrogen atom, a (C3-C10)-heterocyclic ring;
    wherein $R_6$ is optionally substituted with up to 3 J substituents;
  wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;
V is O or a valence bond; and
T is:
  (C1-C12)-aliphatic-;
  (C6-C10)-aryl-,
  (C6-C10)-aryl-(C1-C12)aliphatic-,
  (C3-C10)-cycloalkyl or -cycloalkenyl-,
  [(C3-C10)-cycloalkyl or -cycloalkenyl]-(C1-C12)-aliphatic-,
  (C3-C10)-heterocyclyl-,
  (C3-C10)-heterocyclyl-(C1-C12)-aliphatic-,
  (C5-C10)-heteroaryl-, or
  (C5-C10)-heteroaryl-(C1-C12)-aliphatic-;
    wherein up to 3 aliphatic carbon atoms in T may be replaced by a heteroatom selected from O, N, NH, S, SO, or $SO_2$ in a chemically stable arrangement;
    wherein each T is optionally substituted with up to 3 J substituents;
provided that the following compounds are excluded:
  a) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester glycine;
  b) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
  c) N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
  d) N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
  e) N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
  f) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-1,1-dimethylethyl ester, glycine;
  g) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycine;
  h) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-2-phenyl-glycinamide;
  i) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N,N-dimethyl-2-phenyl-glycinamide;
  j) (2S)—N-acetyl-L-leucyl-(2S)-2-cyclohexylglycyl-(3S)-6,10-dithia-2-azaspiro[4.5]decane-3-carbonyl-3-amino-2-oxohexanoylglycyl-N-methoxy-N-methyl-2-phenyl-glycinamide;
  k) N-acetyl-L-α-glutamyl-L-α-glutamyl-L-valyl-L-valyl-N-[1-[oxo(2-propenylamino)acetyl]butyl]-,bis(1,1-dimethylethyl)ester-(8S)-1,4-dithia-7-azaspiro[4.4]nonane-8-carboxamide;
  l) N-acetyl-L-α-glutamyl-L-α-glutamyl-L-valyl-L-valyl-N-[1-[oxo(2-propenylamino)acetyl]butyl]-,2-(1,1-dimethylethyl)ester-(8S)-1,4-dithia-7-azaspiro[4.4]nonane-8-carboxamide;
  m) N-acetyl-L-α-glutamyl-L-α-glutamyl-L-valyl-L-valyl-N-[1-[oxo(2-propenylamino)acetyl]butyl]-(8S)-1,4-dithia-7-azaspiro[4.4]nonane-8-carboxamide;
  n) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-glycine;
  o) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoylglycyl-2-phenyl-glycinamide;
  p) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-,1,2-bis(1,1-dimethylethyl)-7-(2-propenyl)ester glycine; and q) N-acetyl-L-α-glutamyl-L-α-glutamyl-L-valyl-2-cyclohexylglycyl-(8S)-1,4-dithia-7-azaspiro[4.4]nonane-8-carbonyl-3-amino-2-oxohexanoyl-1,2-bis(1,1-dimethylethyl)ester glycine.

According to another embodiment of the present invention, the compounds are of formula Ia:

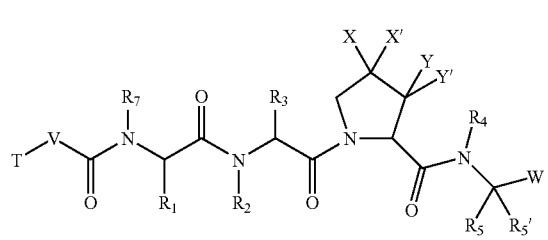

Ia or a pharmaceutically acceptable salt thereof,
wherein:

X and X' are independently C(H), N, NH, O, or S; and X and X' are taken together with the carbon atom to which they are bound to form a 5- to 7-membered saturated or partially unsaturated spirocyclic ring having up to 4 heteroatoms independently selected from N, NH, O, S, SO, and $SO_2$; wherein any atom is optionally singly or multiply substituted with up to 3 substituents selected independently from J; and wherein said ring is optionally fused to a second ring selected from (C6-C10)aryl, (C5-C10)heteroaryl, (C3-C10)cycloalkyl, and a (C3-C10)heterocyclyl, wherein said second ring has up to 3 substituents selected independently from J;

J is halogen, —OR', —$NO_2$, —CN, —$CF_3$, —$OCF_3$, —R', oxo, thioxo, =N(R'), =N(OR'), 1,2-methylenedioxy, 1,2-ethylenedioxy, —N(R')$_2$, —SR', —SOR', —$SO_2$R', —$SO_2$N(R')$_2$, —$SO_3$R', —C(O)R', —C(O)C(O)R', —C(O)C(O)OR', —C(O)C(O)NR', —C(O)$CH_2$C(O)R', —C(S)R', —C(S)OR', —C(O)OR', —OC(O)R', —C(O)N(R')$_2$, —OC(O)N(R')$_2$, —C(S)N(R')$_2$, —($CH_2$)$_{0-2}$NHC(O)R', —N(R')N(R')COR', —N(R')N(R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); wherein;

R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' are optionally and independently substituted with J;
wherein two R' groups bound to the same atom form a 3- to 10-membered aromatic or non-aromatic ring having up to 3 heteroatoms independently selected from N, NH, O, S, SO, and $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J;

Y and Y' are hydrogen;

$R_1$ and $R_3$ are independently:
(C1-C6)-aliphatic-,
(C3-C10)-cycloalkyl- or -cycloalkenyl-,
[(C3-C10)-cycloalkyl- or -cycloalkenyl]-(C1-C6)-aliphatic-, or
(C6-C10)-aryl-(C1-C6)aliphatic-;
wherein up to 3 aliphatic carbon atoms in $R_1$ and $R_3$ may be replaced by a heteroatom selected from O, N, NH, S, SO, or $SO_2$ in a chemically stable arrangement;
wherein each of $R_1$ and $R_3$ is independently and optionally substituted with up to 3 substituents independently selected from J;

$R_2$ and $R_7$ are hydrogen;

$R_4$ is selected from:
hydrogen-,
(C1-C6)-alkyl-,
(C3-C10)-cycloalkyl-(C1-C6)-aliphatic-, or
(C6-C10)-aryl-(C1-C6)-aliphatic-;
wherein $R_4$ is independently and optionally substituted with up to 3 substituents independently selected from J;

$R_5$, is hydrogen;

$R_5$ is (C1-C6)-aliphatic, wherein any hydrogen is optionally replaced with halogen;

W is:

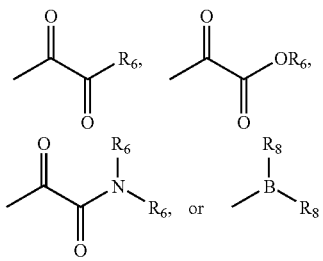

wherein each $R_6$ is independently:
hydrogen-,
(C1-C6)-alkyl-,
(C6-C10)-aryl-,
(C6-C10)-aryl-(C1-C6)alkyl-,
(C3-C10)-cycloalkyl- or cycloalkenyl-,
[(C3-C10)-cycloalkyl- or cycloalkenyl]-(C1-C6)-alkyl-,
(C5-C10)-heteroaryl-(C1-C6)-alkyl-, or
two $R_6$ groups, which are bound to the same nitrogen atom, form together with that nitrogen atom, a (C3-C10)-heterocyclic ring;
wherein $R_6$ is optionally substituted with up to 3 J substituents;
wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;

V is a valence bond; and
T is:
- (C6-C10)-aryl-,
- (C6-C10)-aryl-(C1-C6)aliphatic-,
- (C5-C10)-heteroaryl-, or
- (C5-C10)-heteroaryl-(C1-C6)-aliphatic-;
  wherein up to 3 aliphatic carbon atoms in T may be replaced by a heteroatom selected from O, N, NH, S, SO, or $SO_2$ in a chemically stable arrangement;
  wherein each T is optionally substituted with up to 3 J substituents.

According to one embodiment of compounds of formula I, the

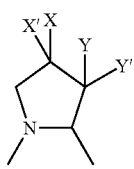

radical is:

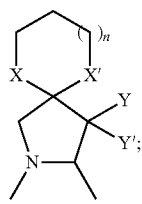

wherein:
- n is 0, 1, or 2;
- Y and Y' are as defined in any of the embodiments herein; and
- the ring containing X and X' is optionally substituted with up to 3 J substituents, wherein J is as defined in any of the embodiments herein.

According to another embodiment for compounds of formula I, the

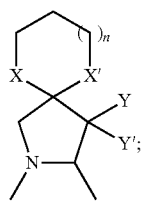

radical is:

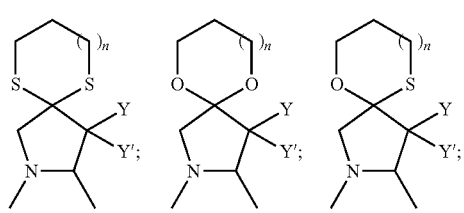

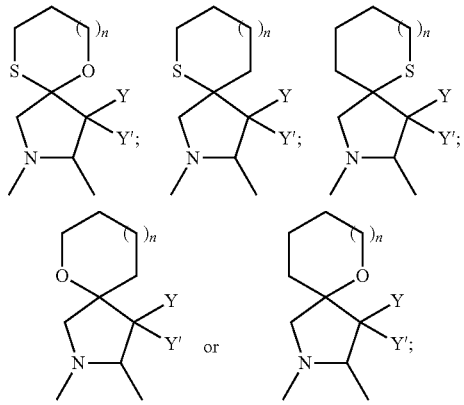

wherein:
- n is 0, 1, or 2;
- Y and Y' are as defined above; and the ring containing X and X' is optionally substituted with up to 3 J substituents, wherein J is as defined in any of the embodiments herein.

According to another embodiment for compounds of formula I, the

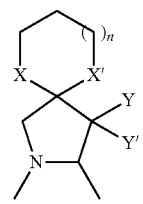

radical is:

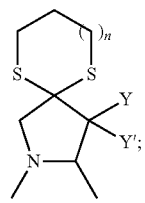

wherein:
- n is 0 or 1; and
- Y and Y' are H.

In another embodiment of compounds of formula I, the

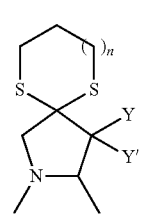

radical is:

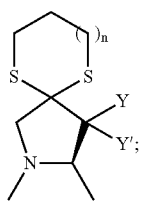

wherein:
n is 0 or 1; and
Y and Y' are H.

In another embodiment of compounds of formula I, the

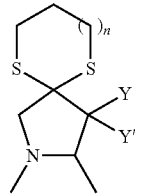

radical is:

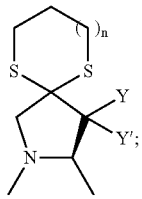

wherein:
n is 1; and
Y and Y' are H.

According to one embodiment of compounds of formula Ia, the

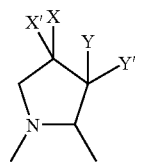

radical is:

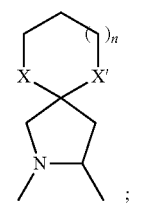

wherein:
n is 0, 1, or 2; and
the ring containing X and X' is optionally substituted with up to 3 J substituents, wherein J is as defined in any of the embodiments herein.

According to another embodiment of compounds of formula Ia, the

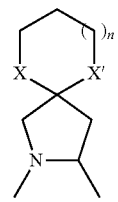

radical is:

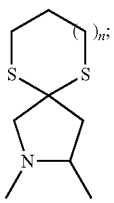 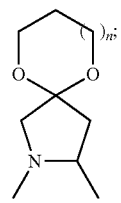 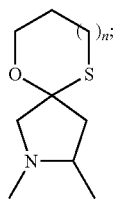

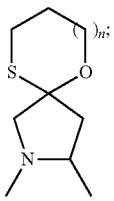 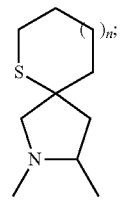 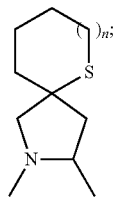

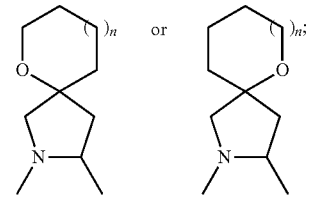

wherein:
n is 0, 1, or 2; and
the ring containing X and X' is optionally substituted with up to 3 J substituents, wherein J is as defined in any of the embodiments herein.

According to another embodiment of compounds of formula Ia, the

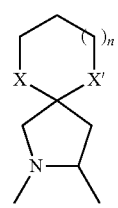

radical is:

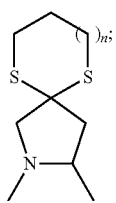

wherein:
n is 0 or 1.

According to another embodiment of compounds of formula Ia, the

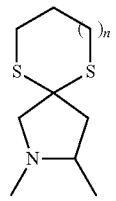

radical is:

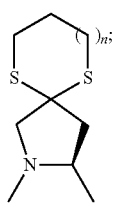

wherein:
n is 0 or 1.

According to another embodiment of compounds of formula I or formula Ia, the present invention provides a compound of formula ID:

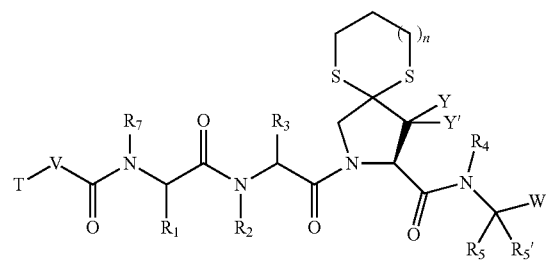

wherein:
n, $R_1$, $R_2$, $R_3$, $R_4$, $R_5$, $R_{5'}$, $R_7$, V, T, W, Y, and Y' are as defined in any of the embodiments herein.

According to an embodiment of compounds of formula I, the

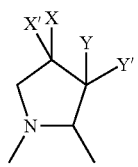

radical is:

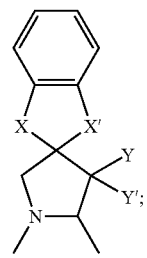

wherein:
X, X', Y, and Y' are as defined in any of the embodiments herein; and
the fused benzo ring is optionally substituted with up to 3 J substituents, wherein J is as defined in any of the embodiments herein.

According to another embodiment of compounds of formula I, the

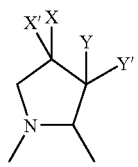

radical is:

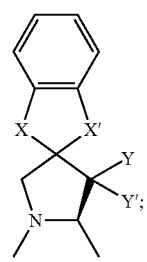

wherein:
X and X', are as defined in any of the embodiments herein;
Y and Y' are H; and
the fused benzo ring is optionally substituted with up to 3 J substituents, wherein J is as defined in any of the embodiments herein.

According to an embodiment of compounds of formula Ia, the

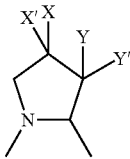

radical is:

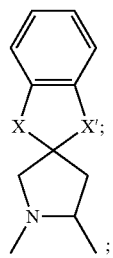

wherein:
X, and X', are as defined in any of the embodiments herein; and
the fused benzo ring is optionally substituted with up to 3 J substituents, wherein J is as defined in any of the embodiments herein.

According to another embodiment of compounds of formula Ia, the

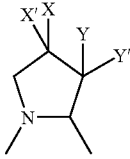

radical is:

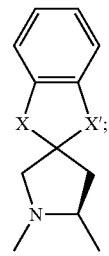

wherein:
X and X', are as defined in any of the embodiments herein;
Y and Y' are H; and
the fused benzo ring is optionally substituted with up to 3 J substituents, wherein J is as defined in any of the embodiments herein.

According to another embodiment of compounds of formula I or formula Ia, the present invention provides a compound of formula IE:

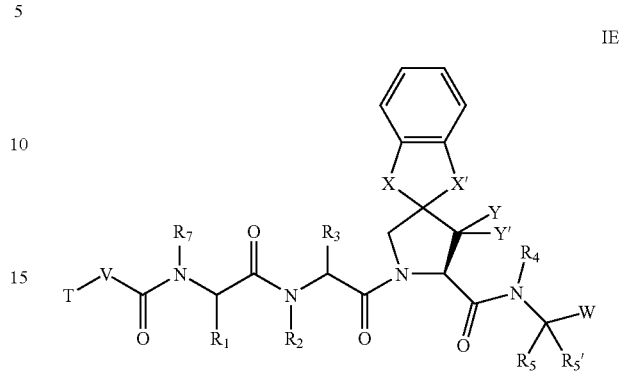

wherein:
$R_1, R_2, R_3, R_4, R_5, R_{5'}, R_7, V, T, W, Y, Y', X$ and $X'$ are as defined in any of the embodiments herein; and
the fused benzo ring is optionally substituted with up to 3 J substituents, wherein J is as defined in any of the embodiments herein.

According to another embodiment for compounds of formula IE, X and X' are S, Y and Y' are H, $R_1, R_2, R_3, R_4, R_5, R_{5'}, R_7, V, T,$ and W are as defined in any of the embodiments herein, and the fused benzo ring is optionally substituted with up to 3 J substituents, wherein J is as defined in any of the embodiments herein.

According to another embodiment for compounds of formula I, the

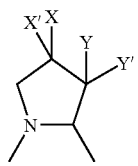

radical is:

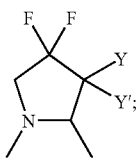

wherein:
Y and Y' are H.

In another embodiment of compounds of formula I, the

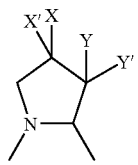

radical is:

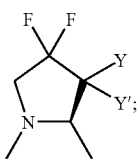

wherein:

Y and Y' are H.

According to yet another embodiment of compounds of formula I, the present invention provides a compound of formula IF:

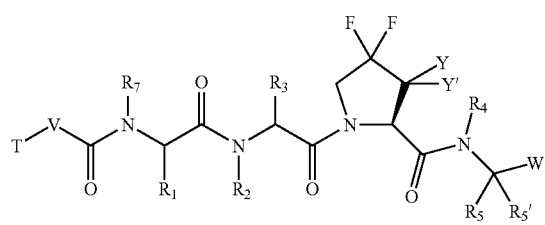

IF wherein:

$R_1$, $R_2$, $R_3$, $R_4$, $R_5$, $R_{5'}$, $R_7$, V, T, W, Y and Y' are as defined in any of the embodiments herein.

According to another embodiment of compounds of formula I, W is:

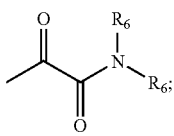

wherein in the W, the $NR_6R_6$ is selected from —NH—(C1-C6 aliphatic), —NH—(C3-C6 cycloalkyl), —NH—CH(CH$_3$)-aryl, or —NH—CH(CH$_3$)-heteroaryl, wherein said aryl or said heteroaryl is optionally substituted with up to 3 halogens.

According to another embodiment of compounds of formula I, W is:

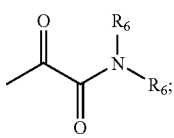

wherein in the W, when the $NR_6R_6$ is selected from —NH—(C1-C6 aliphatic), said C1-C6 aliphatic is C1-C6 alkyl with no J substituents.

According to another embodiment of compounds of formula I, W is:

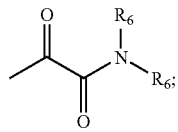

wherein in the W, when the $NR_6R_6$ is selected from either (C6-C10)-aryl-(C1-C12)-aliphatic or (C5-C10)-heteroaryl-(C1-C12)-aliphatic-, said C1-C12-aliphatic is a C1-C6 alkyl group with no J substituents. In another embodiment, said C1-C6 alkyl is substituted with up to 3 J substituents.

According to another embodiment in compounds of formula I, the $NR_6R_6$ in the W radical is:

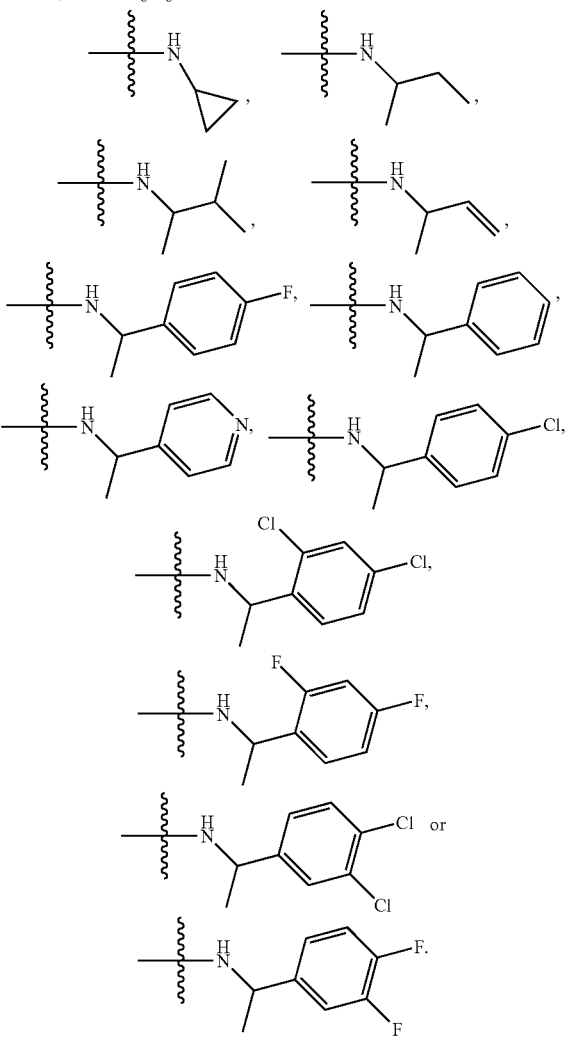

According to another embodiment in compounds of formula I, the $NR_6R_6$ in the W radical is:

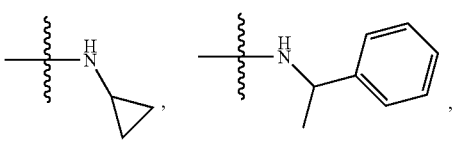

-continued

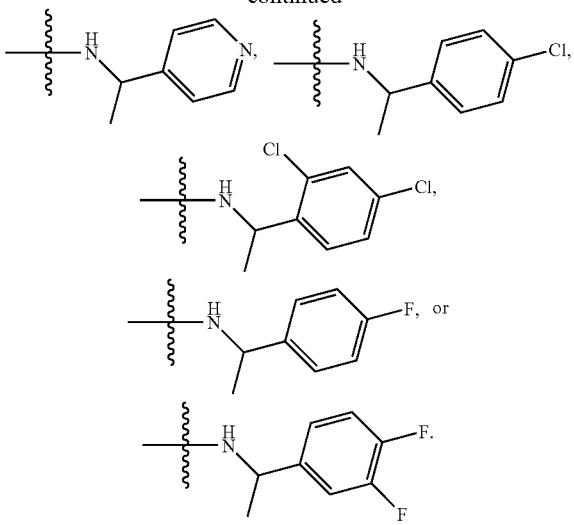

In another embodiment of compounds of formula I, in the W, the NR$_6$R$_6$ is:

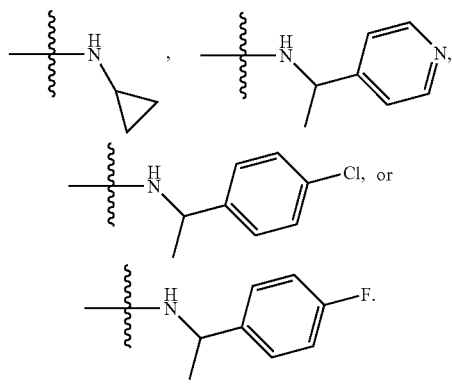

In yet another embodiment of compounds of formula I, in the W, the NR$_6$R$_6$ is:

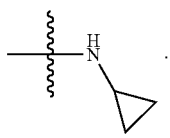 [SMILES: *NC1CC1]

According to an embodiment in compounds of formula I or formula Ia, the NR$_6$R$_6$ in the W radical is:

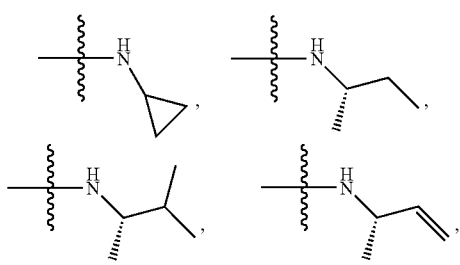

-continued

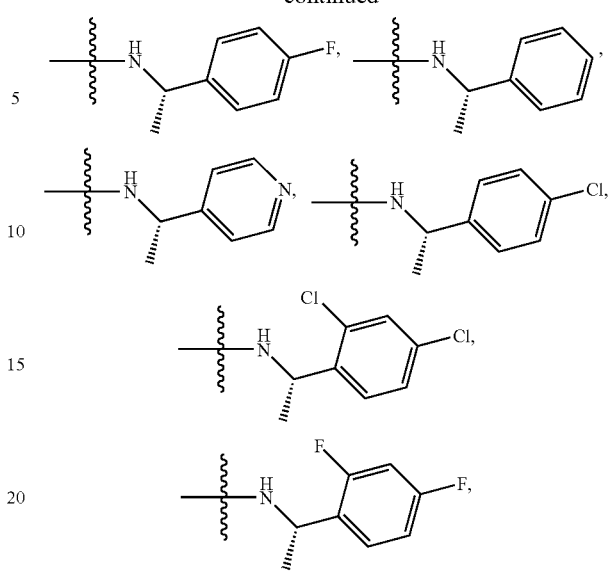

According to another embodiment in compounds of formula I or formula Ia, the NR$_6$R$_6$ in the W radical is:

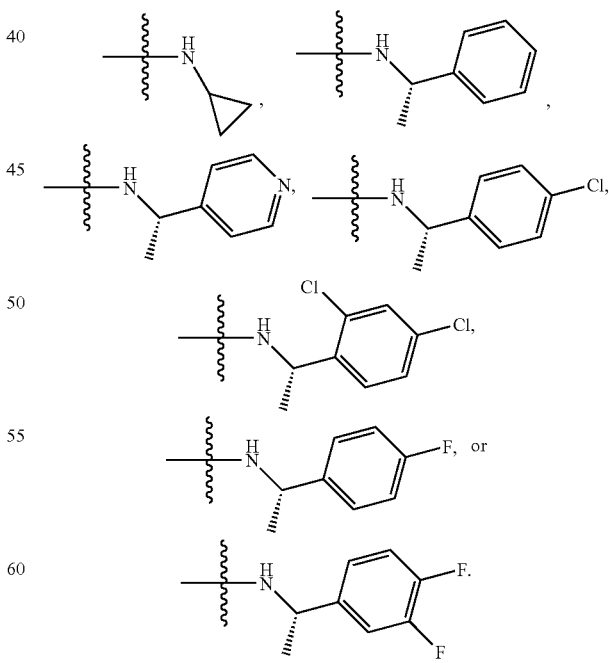

In another embodiment of compounds of formula I or formula Ia, in the W, the NR$_6$R$_6$ is:

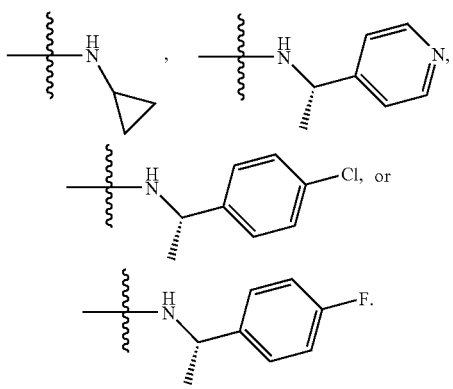

According to another embodiment of compounds of formula I, W is:

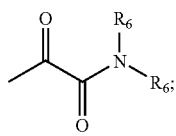

wherein in the W, the $NR_6R_6$ is $NH_2$.

According to another embodiment of compounds of formula I, W is:

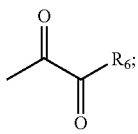

wherein in the W, the $R_6$ is as defined in any of the embodiments herein.

According to another embodiment of compounds of formula I, W is:

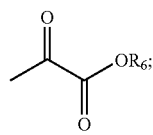

wherein in the W, the $R_6$ is as defined in any of the embodiments herein.

According to another embodiment of compounds of formula I, W is:

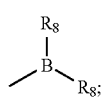

wherein in the W, the $R_8$ is as defined in any of the embodiments herein.

According to an embodiment of compounds of formula Ia, W is:

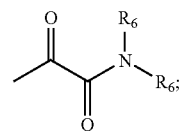

wherein in the W, the $NR_6R_6$ is selected from —NH—(C1-C6 aliphatic), —NH—(C3-C6 cycloalkyl), —NH—CH(CH$_3$)-aryl, or —NH—CH(CH$_3$)-heteroaryl, wherein said aryl or said heteroaryl is optionally substituted with up to 3 halogens.

According to another embodiment of compounds of formula Ia, W is:

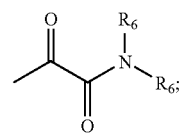

wherein in the W, when the $NR_6R_6$ is selected from —NH—(C1-C6 alkyl), said C1-C6 alkyl has no J substituents.

According to another embodiment of compounds of formula Ia, W is:

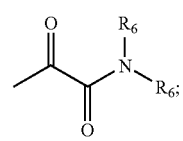

wherein in the W, when the $NR_6R_6$ is selected from either (C6-C10)-aryl-(C1-C6)-alkyl or (C5-C10)-heteroaryl-(C1-C6)-alkyl-, said C1-C6 alkyl group has no J substituents. In another embodiment, said C1-C6 alkyl is substituted with up to 3 J substituents.

According to another embodiment in compounds of formula Ia, the $NR_6R_6$ in the W radical is:

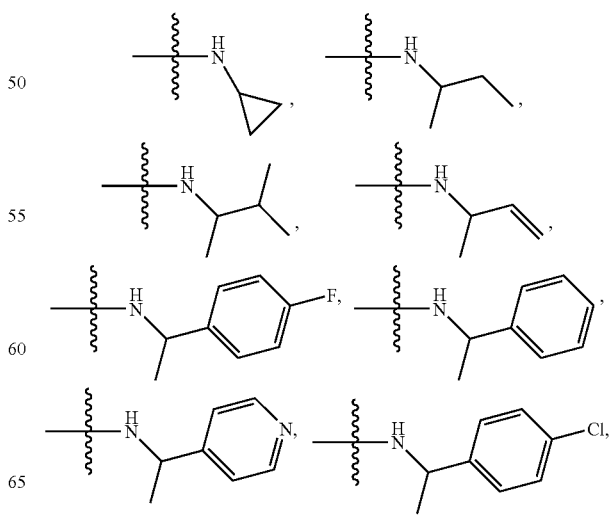

-continued

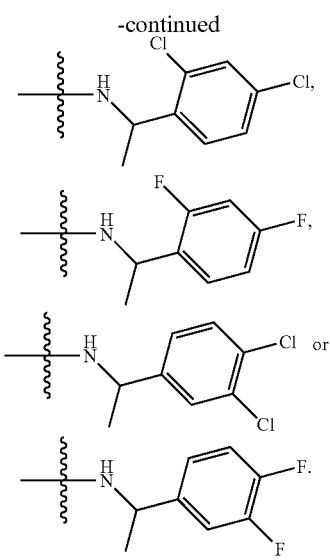

According to another embodiment in compounds of formula Ia, the $NR_6R_6$ in the W radical is:

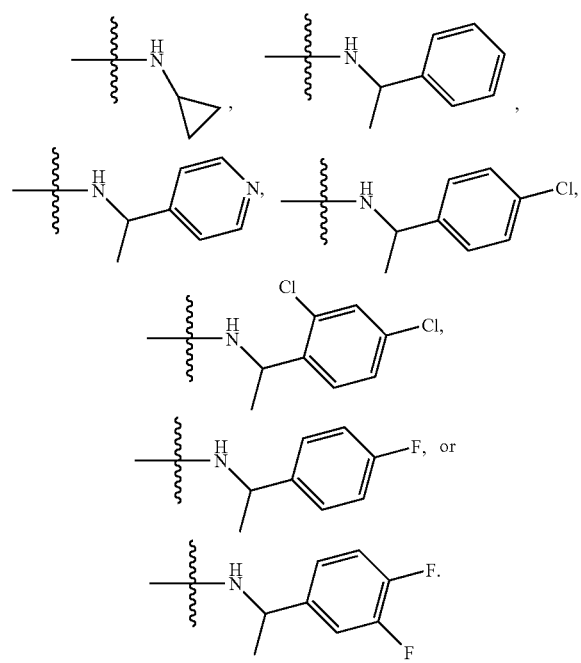

In another embodiment of compounds of formula Ia, in the W, the $NR_6R_6$ is:

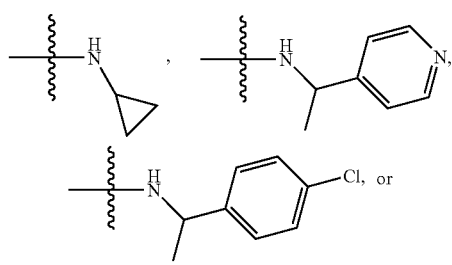

-continued

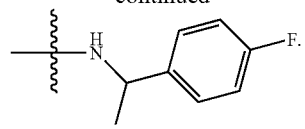

In yet another embodiment of compounds of formula Ia, in the W, the $NR6R_6$ is:

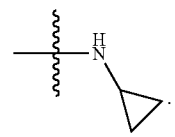 [SMILES: *NC1CC1]

According to another embodiment of compounds of formula Ia, W is:

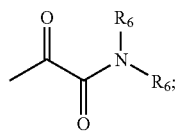

wherein in the W, the $NR_6R_6$ is $NH_2$.

According to another embodiment of compounds of formula Ia, W is:

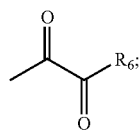

wherein in the W, the $R_6$ is as defined in any of the embodiments herein.

According to another embodiment of compounds of formula Ia, W is:

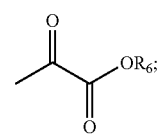

wherein in the W, the $R_6$ is as defined in any of the embodiments herein.

According to another embodiment of compounds of formula Ia, W is:

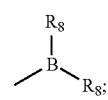

wherein in the W, the $R_8$ is as defined in any of the embodiments herein.

According to another embodiment for W in compounds of formula I or formula Ia, each $R_8$ together with the boron atom, is a (C5-C10)-membered heterocyclic ring having no additional heteroatoms other than the boron and the two oxygen atoms. In one embodiment, groups are selected from:

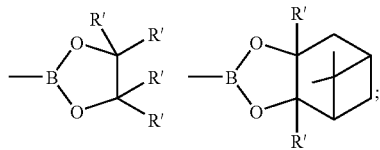

wherein R' is (C1-C6)-aliphatic. In another embodiment of compounds of formula I or formula IA, R' is methyl.

According to yet another embodiment of compounds of formula I, the present invention provides a compound of formula IG:

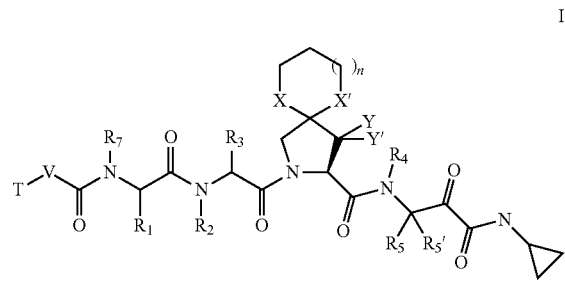

IG wherein:

n, $R_1$, $R_2$, $R_3$, $R_4$, $R_5$, $R_{5'}$, $R_7$, V, T, X, X', Y, and Y' are as defined in any of the embodiments herein.

According to another embodiment for compounds of formula IG, X and X' are S, Y and Y' are H, n, $R_1$, $R_2$, $R_3$, $R_4$, $R_5$, $R_{5'}$, $R_7$, V, and T are as defined in any of the embodiments herein.

According to another embodiment of compounds of formula I or formula Ia, the present invention provides a compound of formula IG-1:

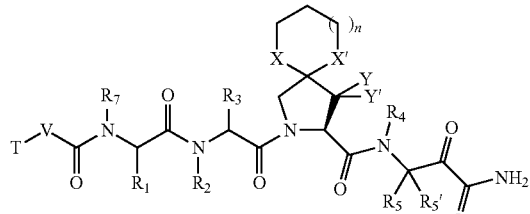

IG-1 wherein:

n, $R_1$, $R_2$, $R_3$, $R_4$, $R_5$, $R_{5'}$, $R_7$, V, T, X, X', Y, and Y' are as defined in any of the embodiments herein.

According to another embodiment of compounds of formula IG-1, X and X' are S, Y and Y' are H, n, $R_1$, $R_2$, $R_3$, $R_4$, $R_5$, $R_{5'}$, $R_7$, V, and T are as defined in any of the embodiments herein.

According to another embodiment in compounds of formula I, $R_{5'}$ is hydrogen and $R_5$ is:

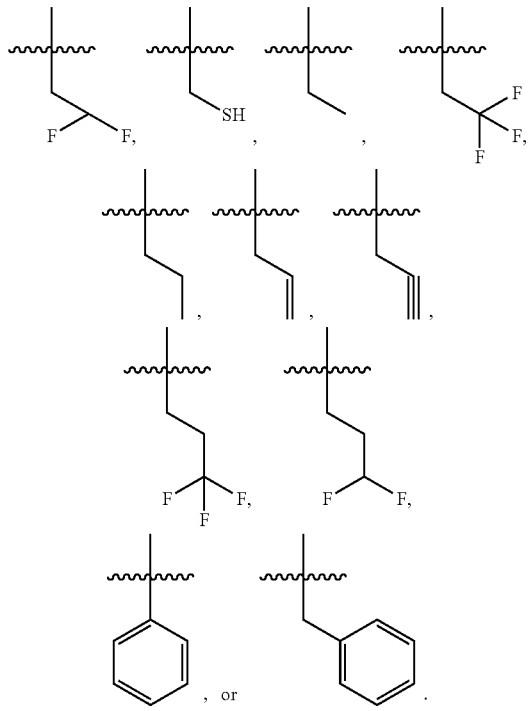

, or

According to yet another embodiment in compounds of formula I, $R_{5'}$ is hydrogen and $R_5$ is:

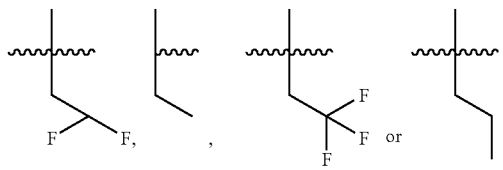

According to another embodiment in compounds of formula I, $R_{5'}$ and $R_5$ is:

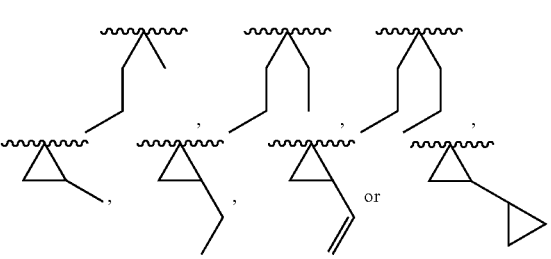

According to an embodiment in compounds of formula Ia, $R_5$ is:

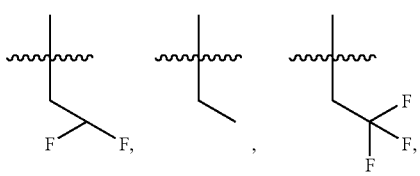

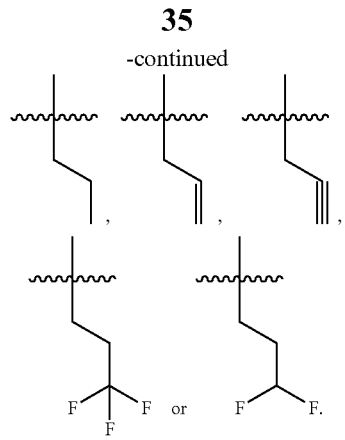

According to another embodiment in compounds of formula Ia, $R_5$ is:

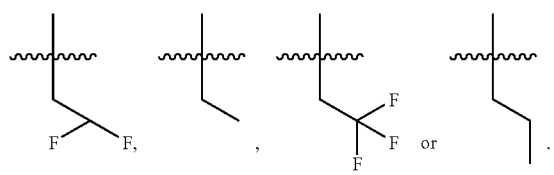

According to another embodiment of compounds of formula I or formula Ia, the present invention provides a compound of formula IH:

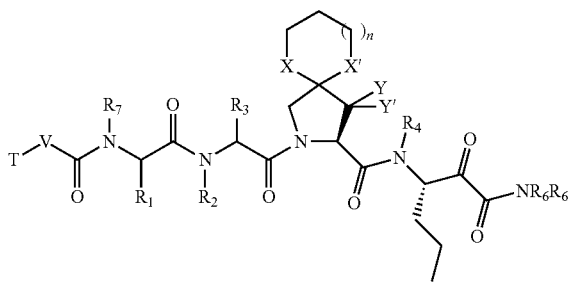

IH wherein:

n, $R_1$, $R_2$, $R_3$, $R_4$, each $R_6$, $R_7$, V, T, X, X', Y, and Y' are as defined in any of the embodiments herein.

According to another embodiment for compounds of formula IH, n, $R_1$, $R_2$, $R_3$, $R_4$, $R_7$, V, and T are as defined in any of the embodiments herein, X and X' are S, Y and Y' are H, and $NR_6R_6$ is:

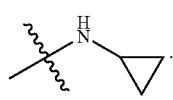 [SMILES: *NC1CC1]

According to another embodiment for compounds of formula IH, n, $R_1$, $R_2$, $R_3$, $R_4$, $R_7$, V, and T are as defined in any of the embodiments herein, X and X' are S, Y and Y' are H, and $NR_6R_6$ is:

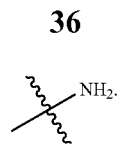

According to another embodiment for compounds of formula I, $R_2$, $R_4$, and $R_7$ are each independently H, methyl, ethyl, or propyl.

According to another embodiment for compounds of formula I, $R_2$, $R_4$, and $R_7$ are each H.

According to an embodiment in compounds of formula Ia, $R_4$ is hydrogen.

According to another embodiment in compounds of formula I or formula Ia, the present invention provides a compound of formula IJ:

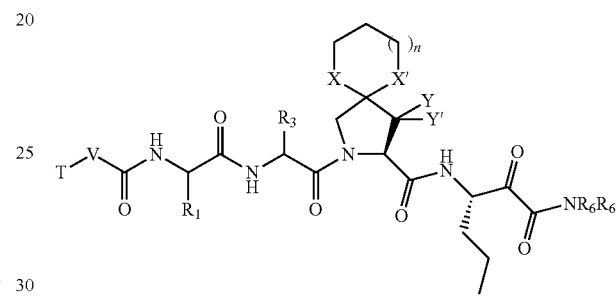

IJ wherein:

n, $R_1$, $R_3$, each $R_6$, V, T, X, X', Y, and Y' are as defined in any of the embodiments herein.

According to another embodiment for compounds of formula IJ, n, $R_1$, $R_3$, V, and T are as defined in any of the embodiments herein, X and X' are S, Y and Y' are H, and $NR_6R_6$ is:

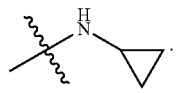

According to another embodiment for compounds of formula IJ, n, $R_1$, $R_3$, V, and T are as defined in any of the embodiments herein, X and X' are S, Y and Y' are H, and $NR_6R_6$ is:

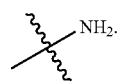

According to another embodiment in compounds of formula I, $R_3$ is:

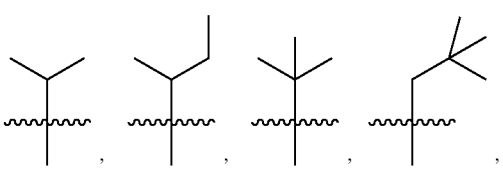

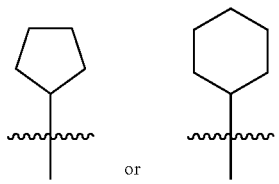

or

In another embodiment in compounds of formula I, R₃ is:

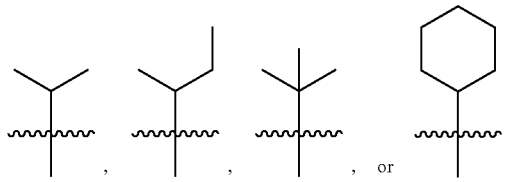

, , , or

According to another embodiment in compounds of formula I, R₃ is:

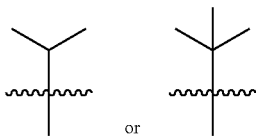

or .

According to an embodiment in compounds of formula Ia, R₃ is:

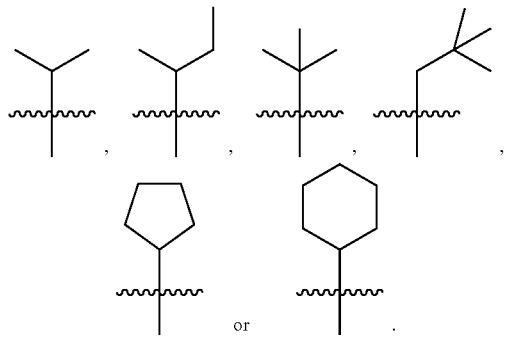

, , , , or .

In another embodiment in compounds of formula Ia, R₃ is:

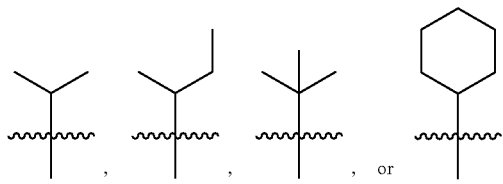

, , , or .

According to another embodiment in compounds of formula Ia, R₃ is:

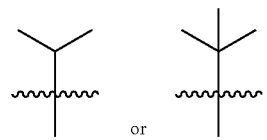

or .

According to another embodiment in compounds of formula I or formula Ia, the present invention provides a compound of formula IK:

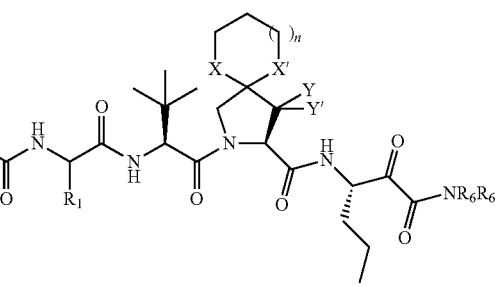

IK wherein:
n, $R_1$, each $R_6$, V, T, X, X', Y, and Y' are as defined in any of the embodiments herein.

According to another embodiment for compounds of formula IK, n, $R_1$, V, and T are as defined in any of the embodiments herein, X and X' are S, Y and Y' are H, and $NR_6R_6$ is:

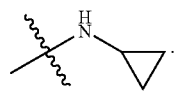

According to another embodiment for compounds of formula IK, n, $R_1$, V, and T are as defined in any of the embodiments herein, X and X' are S, Y and Y' are H, and $NR_6R_6$ is:

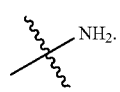

According to another embodiment in compounds of formula I, $R_1$ is:

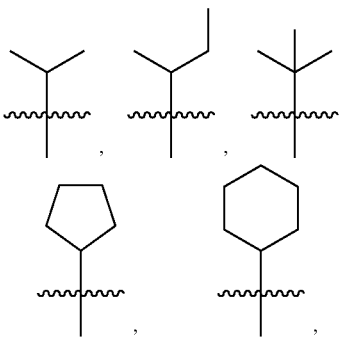

, , ,

, ,

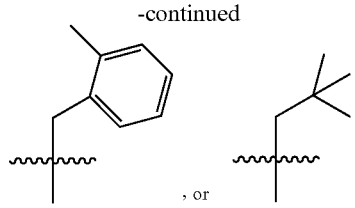
, or .

According to another embodiment in compounds of formula I, R₁ is:

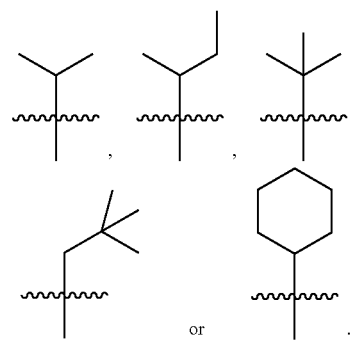
or .

In another embodiment of compounds of formula I, R₁ is cyclohexyl.

According to an embodiment in compounds of formula Ia, R₁ is:

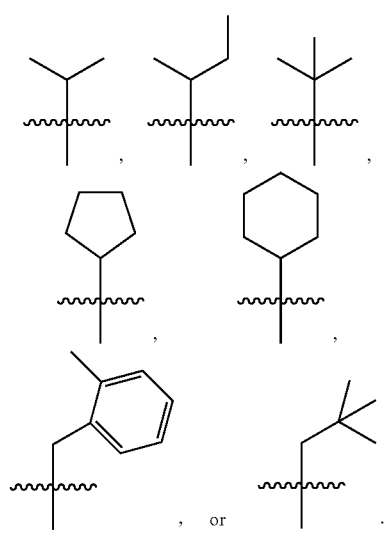
, or .

According to another embodiment in compounds of formula Ia, R₁ is:

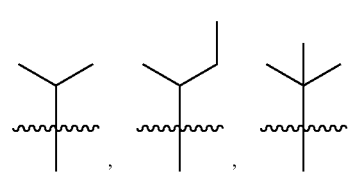
, , ,

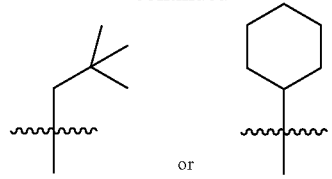
or .

In another embodiment of compounds of formula Ia, R₁ is cyclohexyl.

According to another embodiment of compounds of formula I or formula Ia, the present invention provides a compound of formula IL:

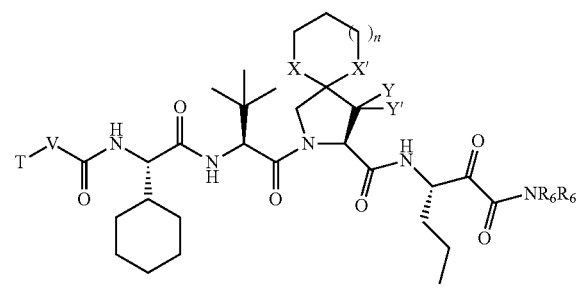

IL wherein:
n, each R₆, V, T, X, X', Y, and Y' are as defined in any of the embodiments herein.

According to another embodiment for compounds of formula IL, n, V, and T are as defined in any of the embodiments herein, X and X' are S, Y and Y' are H, and NR₆R₆ is:

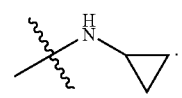
.

According to another embodiment for compounds of formula IL, n, V, and T are as defined in any of the embodiments herein, X and X' are S, Y and Y' are H, and NR₆R₆ is:

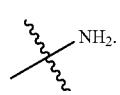
NH₂.

According to another embodiment in compounds of formula I, V is O.

According to another embodiment of compounds of formula I, the present invention provides a compound of formula IM:

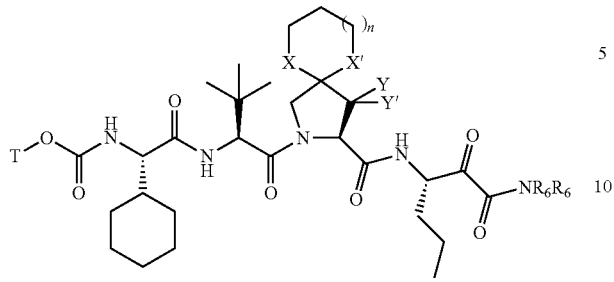

IM wherein:
- n, each $R_6$, T, X, X', Y, and Y' are as defined in any of the embodiments herein.

According to another embodiment for compounds of formula IM, n and T are as defined in any of the embodiments herein, X and X' are S, Y and Y' are H, and $NR_6R_6$ is:

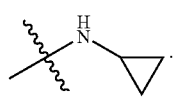

According to another embodiment for compounds of formula IM, n and T are as defined in any of the embodiments herein, X and X' are S, Y and Y' are H, and $NR_6R_6$ is:

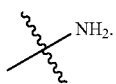

According to another embodiment in compounds of formula I, V is a valence bond.

According to another embodiment in compounds of formula I or formula Ia, the present invention provides a compound of formula IN:

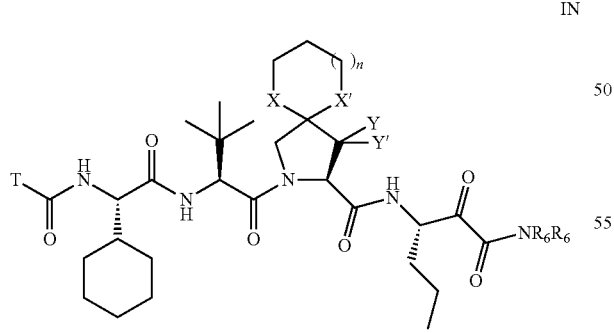

IN wherein:
- n, each $R_6$, T, X, X', Y, and Y' are as defined in any of the embodiments herein.

According to another embodiment for compounds of formula IN, n and T are as defined in any of the embodiments herein, X and X' are S, Y and Y' are H, and $NR_6R_6$ is:

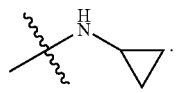

According to another embodiment for compounds of formula IN, n and T are as defined in any of the embodiments herein, X and X' are S, Y and Y' are H, and $NR_6R_6$ is:

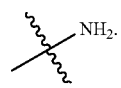

According to an embodiment in compounds of formula I, T is (C3-C10)heterocyclyl- or (C5-C10)heteroaryl-;
  wherein each T is optionally substituted with up to 3 J substituents.

According to another embodiment in compounds of formula I, T is (C5-C6)heterocyclyl- or (C5-C6)heteroaryl-;
  wherein each T is optionally substituted with up to 3 J substituents.

In another embodiment in compounds of formula I, T is:

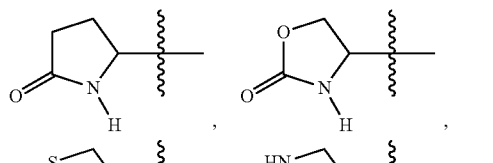

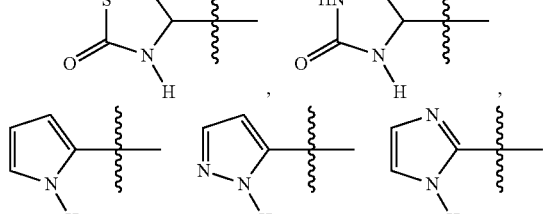

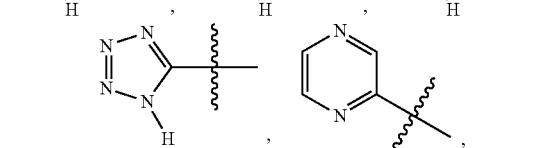

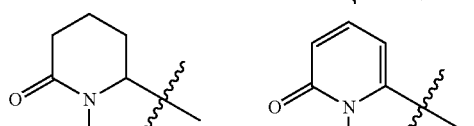

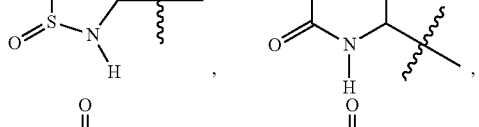

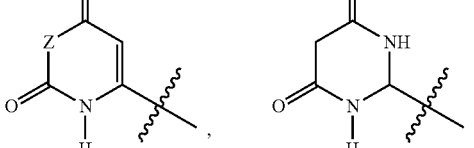

-continued

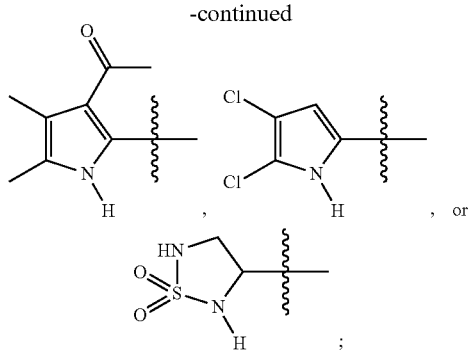

wherein:
Z is independently O, S, NR', or C(R')$_2$.
In another embodiment in compounds of formula I, T is:

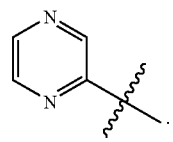 [SMILES: *c1cnccn1]

In another embodiment in compounds of formula I, T is:

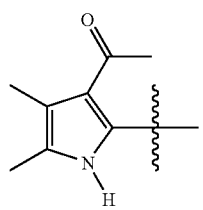

According to an embodiment in compounds of formula Ia, T is:
(C3-C10)heterocyclyl- or (C5-C10)heteroaryl-;
wherein each T is optionally substituted with up to 3 J substituents.

According to another embodiment in compounds of formula Ia, T is (C5-C6)heterocyclyl- or (C5-C6)heteroaryl-;
wherein each T is optionally substituted with up to 3 J substituents.

In another embodiment in compounds of formula Ia, T is:

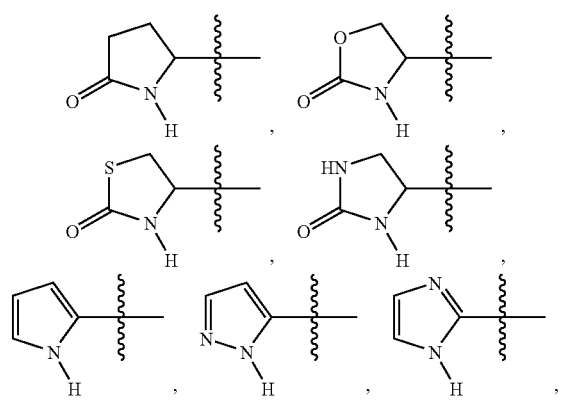

-continued

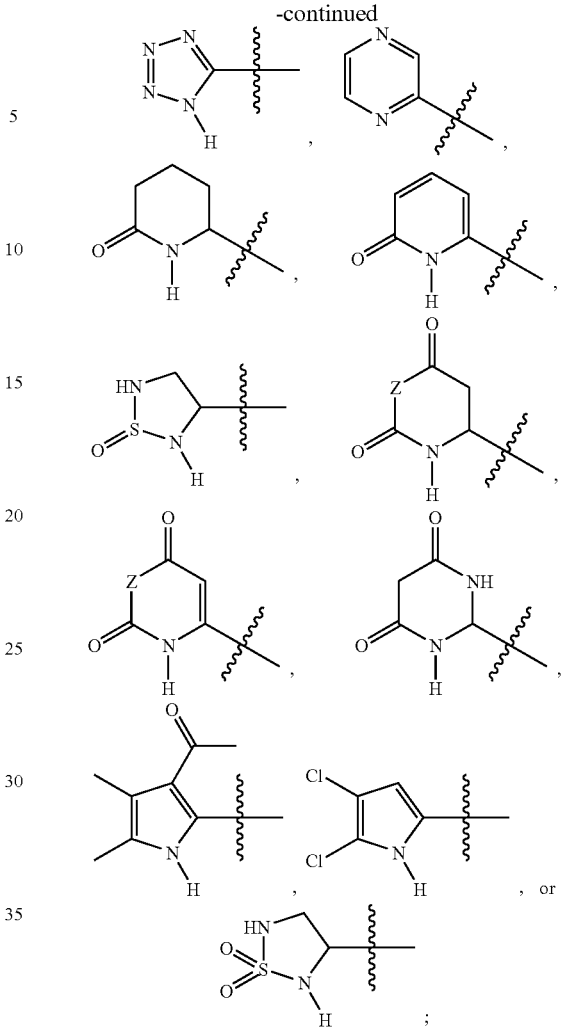

wherein:
Z is independently O, S, NR', or C(R')$_2$.
In another embodiment in compounds of formula Ia, T is:

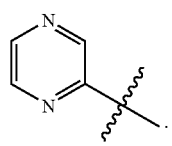 [SMILES: *c1cnccn1]

In another embodiment in compounds of formula Ia, T is:

According to another embodiment of compounds of formula I or formula Ia, the present invention provides a compound of formula IO:

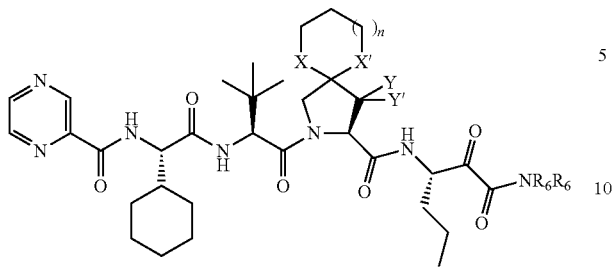

wherein:
n, each $R_6$, X, X', Y, and Y' are as defined in any of the embodiments herein.

According to another embodiment for compounds of formula IN, n is as defined in any of the embodiments herein, X and X' are S, Y and Y' are H, and $NR_6R_6$ is:

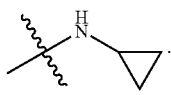

According to another embodiment for compounds of formula IN, n is as defined in any of the embodiments herein, X and X' are S, Y and Y' are H, and $NR_6R_6$ is:

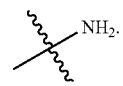

According to another embodiment of compounds of formula I or formula Ia, the present invention provides a compound of formula IP:

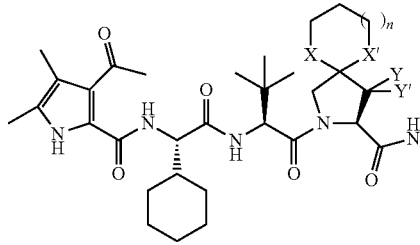

IP wherein:
n, each $R_6$, X, X', Y, and Y' are as defined in any of the embodiments herein.

According to another embodiment for compounds of formula IP, n is as defined in any of the embodiments herein, X and X' are S, Y and Y' are H, and $NR_6R_6$ is:

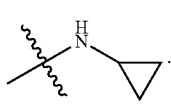

According to another embodiment for compounds of formula IP, n is as defined in any of the embodiments herein, X and X' are S, Y and Y' are H, and $NR_6R_6$ is:

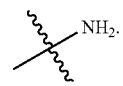

According to an embodiment for compounds of formula I, said (C1-C12)-aliphatic group in R', Y, Y', $R_1$, $R_2$, $R_3$, $R_4$, $R_6$, $R_7$, and T is (C1-C6)-alkyl.

According to an embodiment for compounds of formula Ia, said (C1-C12)-aliphatic group in R' and said (C1-C6)-aliphatic group in $R_1$, $R_3$, $R_5$, and T is (C1-C6)-alkyl.

According to another embodiment in compounds of formula I or formula Ia, the compound is:

1a

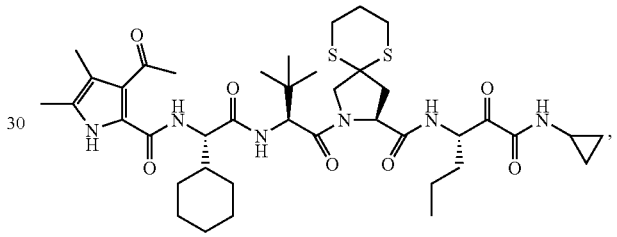

2a

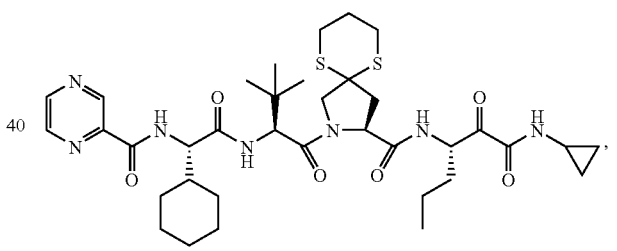

3a

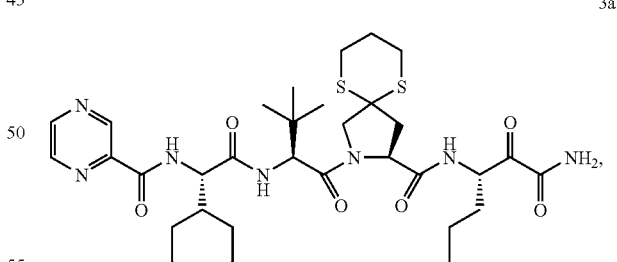

4a

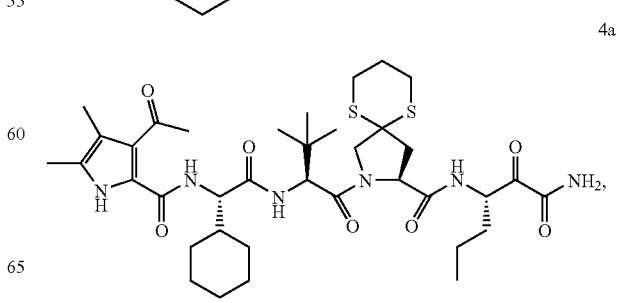

-continued

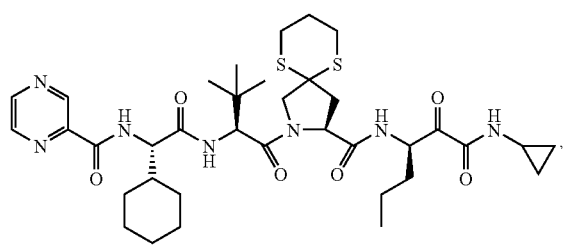

5a

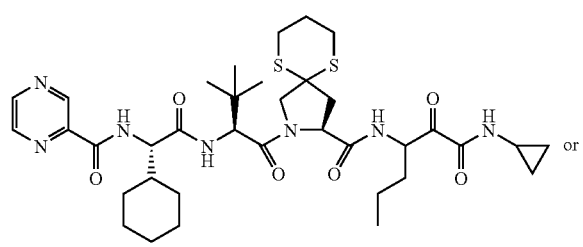

6a or

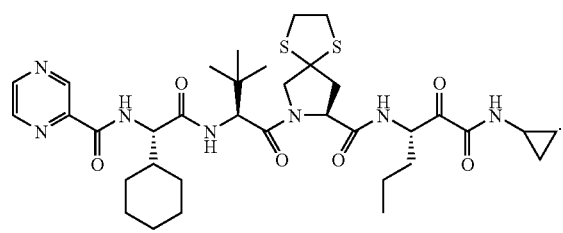

7a

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

In one embodiment, the compounds of this invention have the structure and stereochemistry depicted in formulae ID-IP.

In another embodiment, the compounds of this invention have the structure and stereochemistry depicted in compounds 2a to 4a.

In another embodiment, the compounds of this invention have the structure and stereochemistry depicted in compound 7a.

Any of the embodiments recited above, including those embodiments in the above species, may be combined to produce another embodiment of this invention.

As used herein, P1, P2, P3, P4 refer to the residues of an HCV protease inhibitor as defined in the art [J. A. Landro et al., "Mechanistic Role of an NS4A Peptide Cofactor with the Truncated NS3 Protease of Hepatitis C Virus: Elucidation of the NS4A Stimulatory Effect via Kinetic analysis and Inhibitor Mapping", *Biochemistry*, 36, pp. 9340-9348 (1997)] and as such are well known to skilled practitioners.

The present invention provides potent binders and inhibitors of the HCV NS3/NS4a serine protease. In certain embodiments of compounds of formulae I and Ia of the present invention, the compounds have P4 caps that allow for additional hydrogen bonds with the enzyme backbone. In certain embodiments of the present invention, a P4 cap nitrogen atom and the carbonyl (adjacent to radical V or T in formulae I or Ia) form hydrogen bonds to the main chain carbonyl and NH groups respectively of the Cys-158 residue of the protease enzyme. In certain embodiments of the present invention, another hydrogen bond is formed by the NH moiety (represented by the N—$R_2$ group in formulae I and Ia, wherein $R_2$ is hydrogen) of the P3 group with the protease backbone. These P4 and P3 hydrogen bond interactions optimize the positioning of the P4 and P3 side chains in the HCV NS3/NS4a serine protease binding site. Additionally, the P2 spirocyclic proline group fills the P2 pocket and makes favorable van der Waals contact with the Arg-155 side chain in the HCV NS3/NS4A serine protease enzyme. This invention also provides W groups that bind efficiently to the catalytic site of the HCV NS3/NS4a serine protease located in the P1' pocket.

Abbreviations which are used in the schemes, preparations and the examples that follow are:
THF: tetrahydrofuran
DMF: N,N,-dimethylformamide
EtOAc: ethyl acetate
AcOH: acetic acid
DMAP: dimethylaminopyridine
HOBt: 1-hydroxybenzotriazole hydrate
HOSu: succinic acid
EDC: 1-(3-dimethylaminopropyl)-3-ethylcarbodiimide hydrochloride
$Et_2O$: diethyl ether
BOC: tert-butyloxycarbonyl
Cbz: benzyloxycarbonyl
Chg: cyclohexyl glycine
t-BG: tert-butylglycine
DAST: (diethylamino)sulfur trifluoride
DMSO: dimethyl sulfoxide
DCCA: dichloroacetic acid
DIEA: diisopropylethylamine
MeCN: acetonitrile
TEMPO: 2,2,6,6-tetramethyl-1-piperidinyloxy, free radical)
DMEM: Dulbecco's Modified Eagle's Medium
PBS: phosphate-buffered saline
rt or RT: room temperature
ON: overnight
ND: not determined
MS: mass spectrometry
LC: liquid chromatography
General Synthetic Methodology:

The compounds of this invention may be prepared in general by methods known to those skilled in the art. Schemes 1A, 1B, and 1-6 below illustrate synthetic routes to the compounds of the present invention. Other equivalent schemes, which will be readily apparent to the ordinary skilled organic chemist, may alternatively be used to synthesize various portions of the molecule as illustrated by the general schemes below, and the preparative examples that follow.

Scheme 1:

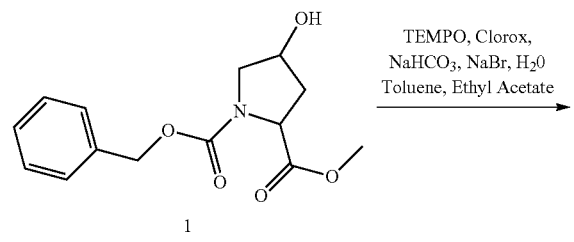

1

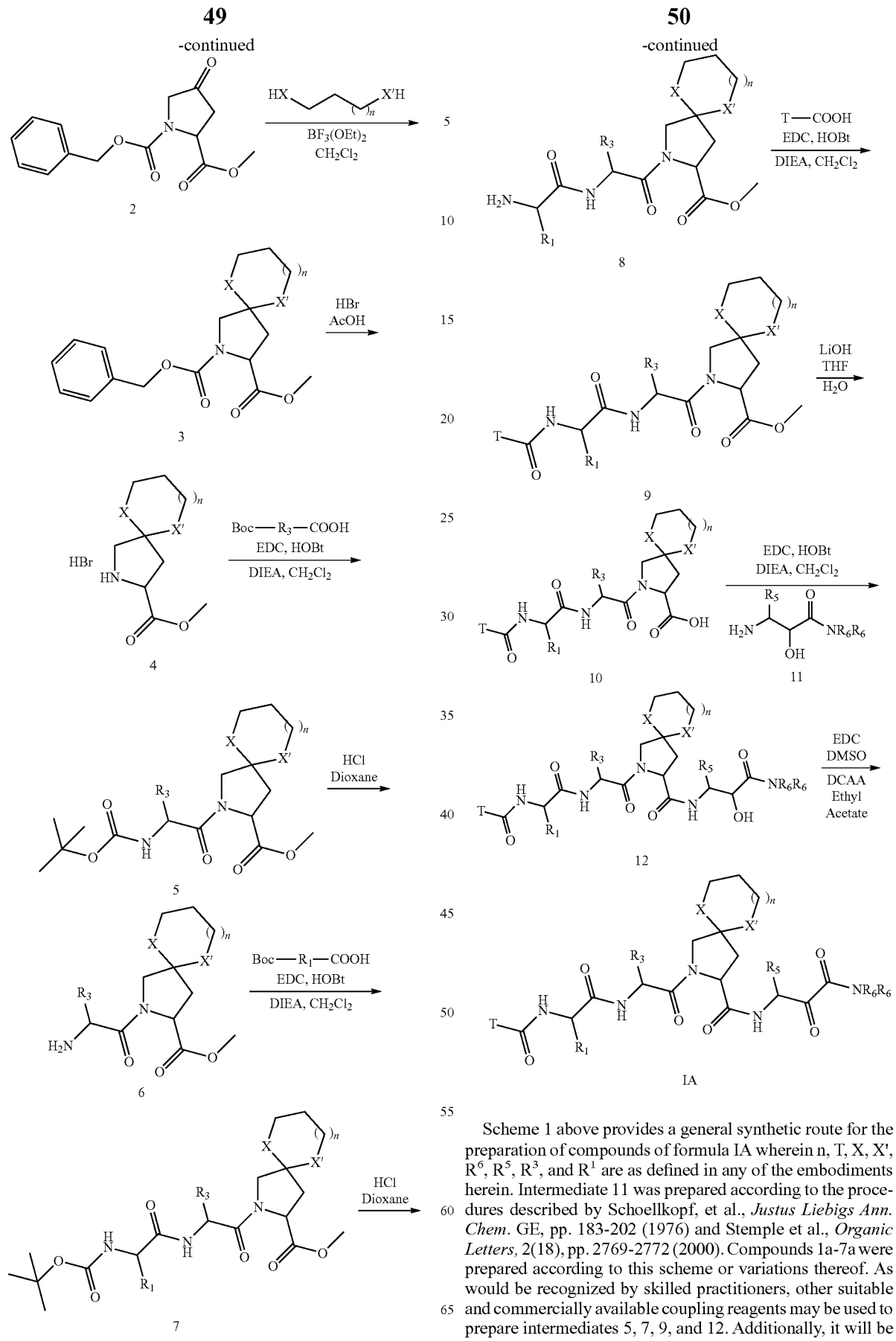

Scheme 1 above provides a general synthetic route for the preparation of compounds of formula IA wherein n, T, X, X', $R^6$, $R^5$, $R^3$, and $R^1$ are as defined in any of the embodiments herein. Intermediate 11 was prepared according to the procedures described by Schoellkopf, et al., *Justus Liebigs Ann. Chem.* GE, pp. 183-202 (1976) and Stemple et al., *Organic Letters*, 2(18), pp. 2769-2772 (2000). Compounds 1a-7a were prepared according to this scheme or variations thereof. As would be recognized by skilled practitioners, other suitable and commercially available coupling reagents may be used to prepare intermediates 5, 7, 9, and 12. Additionally, it will be recognized that the commercially available Boc protected amino acids represented by, for instance, Boc-R₃—COOH, may alternatively be substituted with the commercial Cbz protected amino acids. Suitable deprotection conditions to remove the Cbz protecting groups are known to those skilled in the art. Likewise the oxidation of intermediate 12 to compounds of formula IA can be accomplished using other suitable conditions known to the skilled artisan.

Scheme 1A:

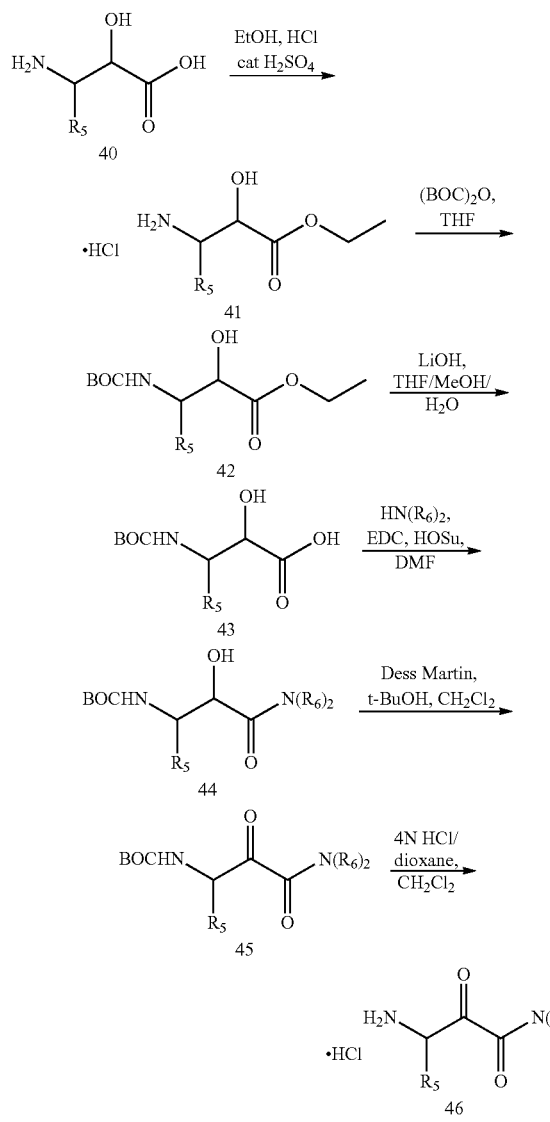

Scheme 1B:

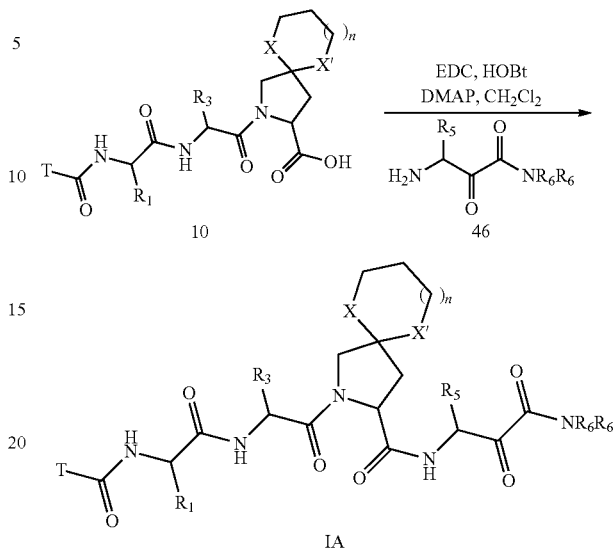

Scheme 1B above provides an alternate synthetic route for the preparation of compounds IA from intermediate 46.

Scheme 2:

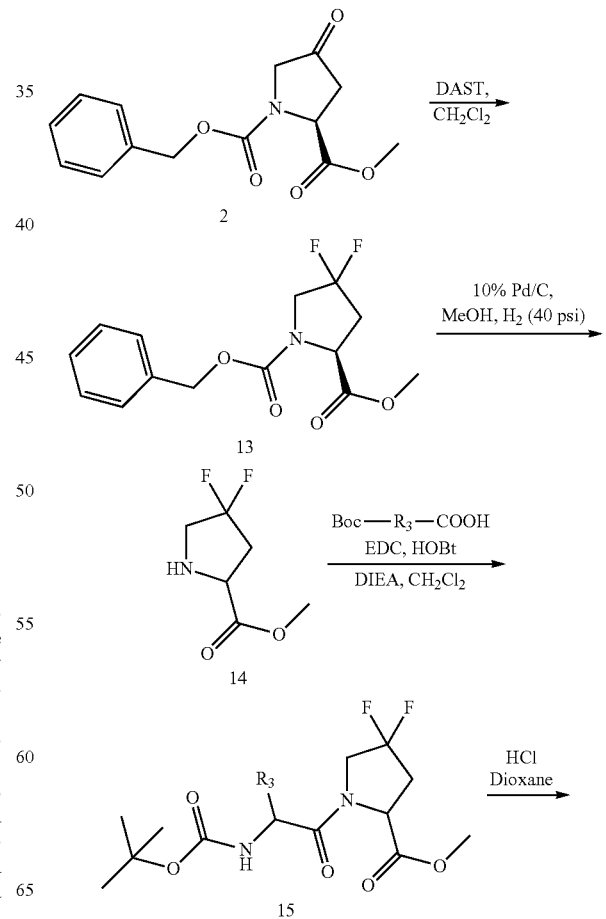

Scheme 1A above provides a synthetic route for the preparation of intermediate 46 from intermediate 40. Intermediate 40 was prepared according to the procedures described by Schoellkopf, et al., *Justus Liebigs Ann. Chem.* GE, pp. 183-202 (1976) and Stemple et al., *Organic Letters*, 2(18), pp. 2769-2772 (2000). Esterification to the ethyl ester hydrochloride 41 was accomplished using catalytic acidic conditions. Boc protection of the amine followed by basic hydrolysis afforded the Boc acid 43. Amine coupling with HN(R₆)₂ with EDC and succinic acid afforded amide 44 which was subsequently oxidized to the diketo amide 45 with Dess-Martin periodinane. Boc removal under acidic conditions provided intermediate 46 as the hydrochloride salt wherein R₅ and R₆ are as defined in any of the embodiments herein.

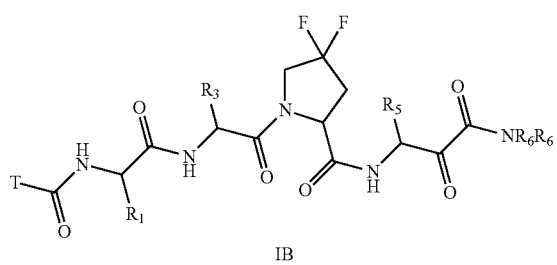

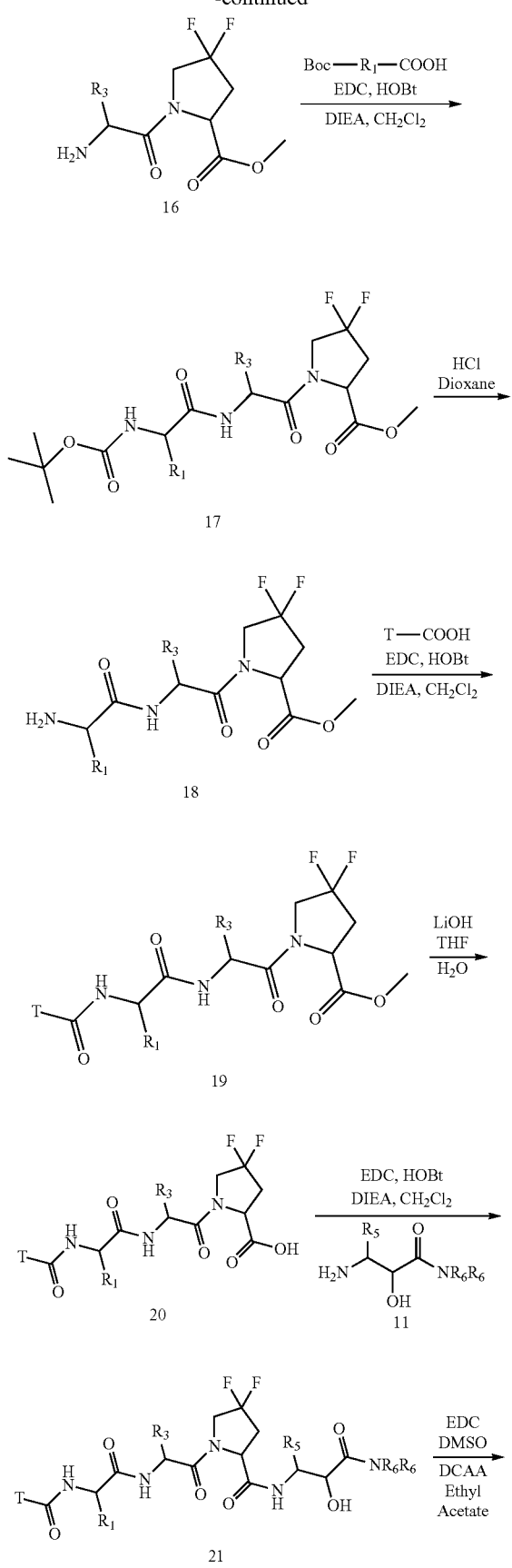

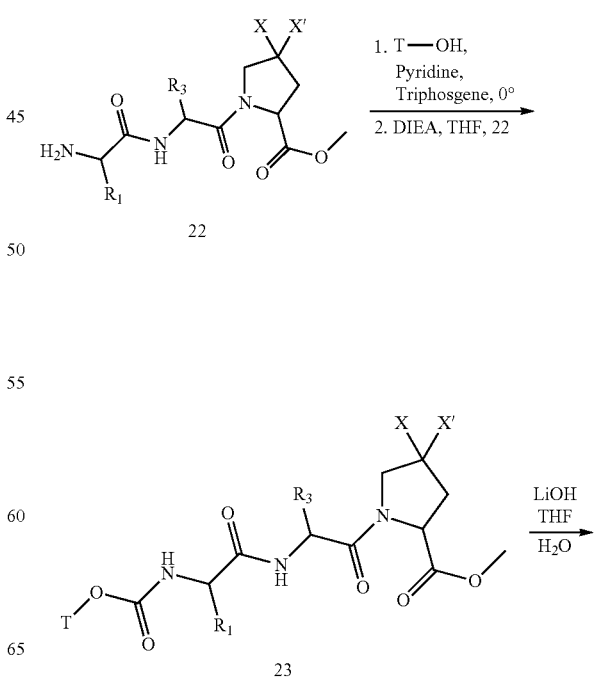

Scheme 2 above provides a general synthetic route for the preparation of compounds of formula IB wherein T, $R^6$, $R^5$, $R^3$, and $R^1$ are as defined in any of the embodiments herein. As would be recognized by skilled practitioners, other suitable and commercially available coupling reagents may be used to prepare intermediates 15, 17, 19, and 21. Additionally, it will be recognized that the commercially available Boc protected amino acids represented by, for instance, Boc-$R_3$—COOH, may alternatively be substituted with the commercial Cbz protected amino acids. Suitable deprotection conditions to remove the Cbz protecting groups are known to those skilled in the art. Likewise the oxidation of intermediate 21 to compounds of formula IB may be accomplished using other suitable conditions known to the skilled artisan. One of skill in the art will also recognize that compounds of formula IB may also be prepared from intermediate 46 using the conditions described above in Scheme 1B.

Scheme 3:

-continued
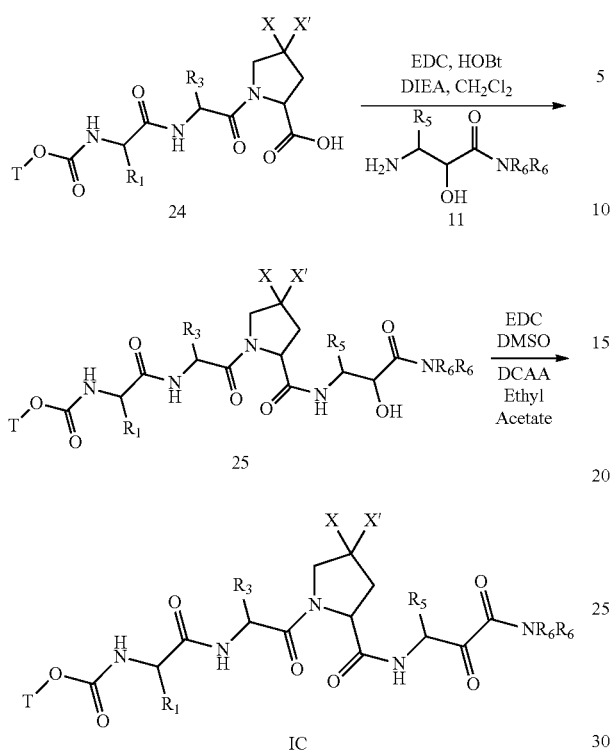
Scheme 3 above provides a general synthetic route for the preparation of compounds of formula IC wherein X, X', T, $R^6$, $R^5$, $R^3$, and $R^1$ are as defined in any of the embodiments herein. One of skill in the art will also recognize that compounds of formula IC may also be prepared from intermediate 46 using the conditions described above in Scheme 1B.
Scheme 4:
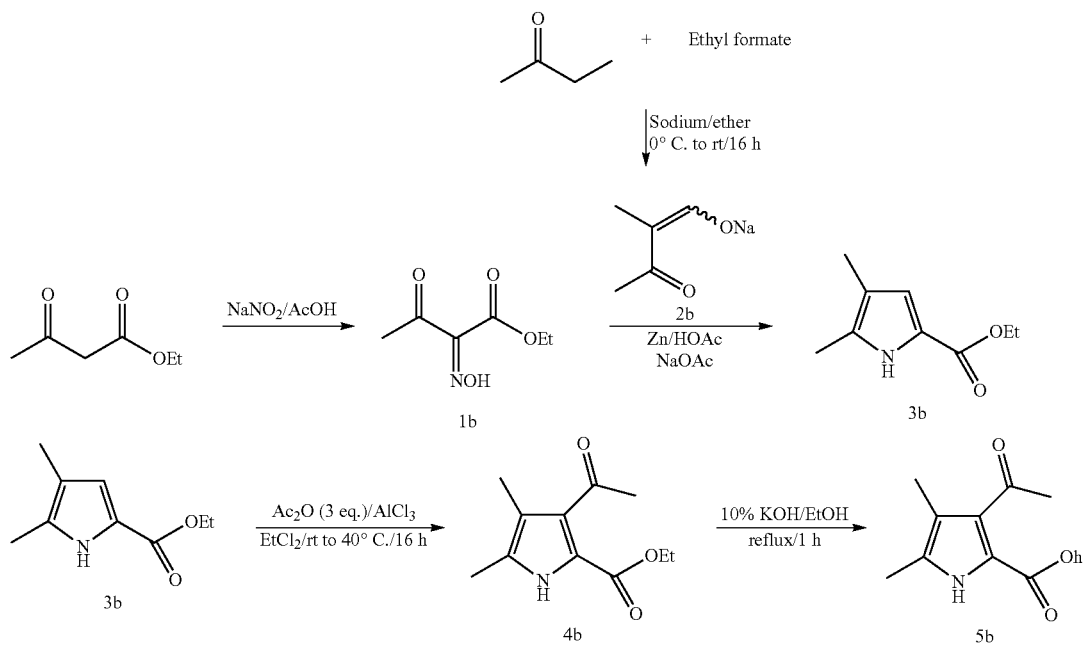

Scheme 4 above provides a synthetic route for the preparation of pyrrole acid intermediate 5b. It will be appreciated by those skilled in the art that other pyrrole analogs of interest may be synthesized by modifications of scheme 4.
Scheme 5:
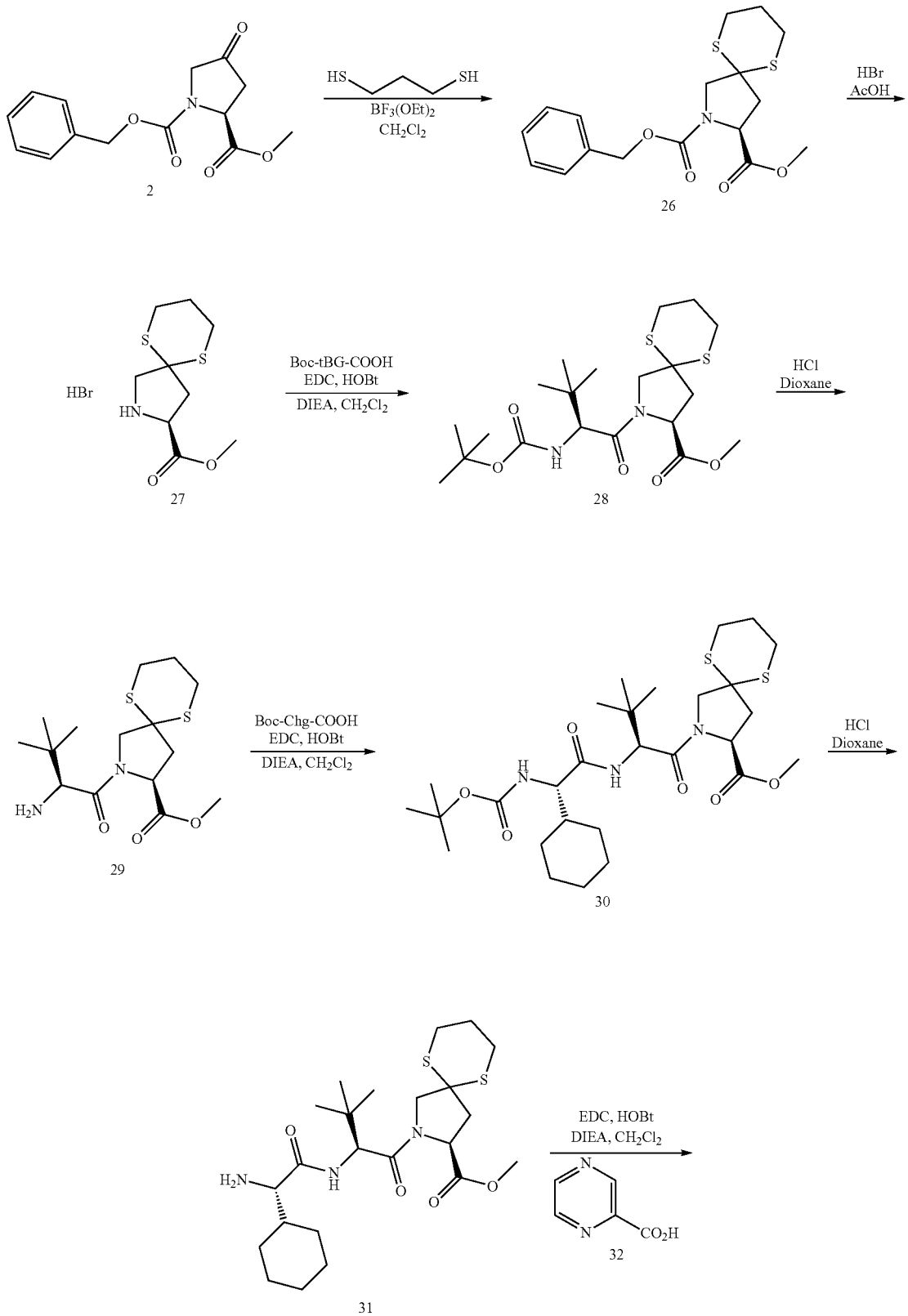

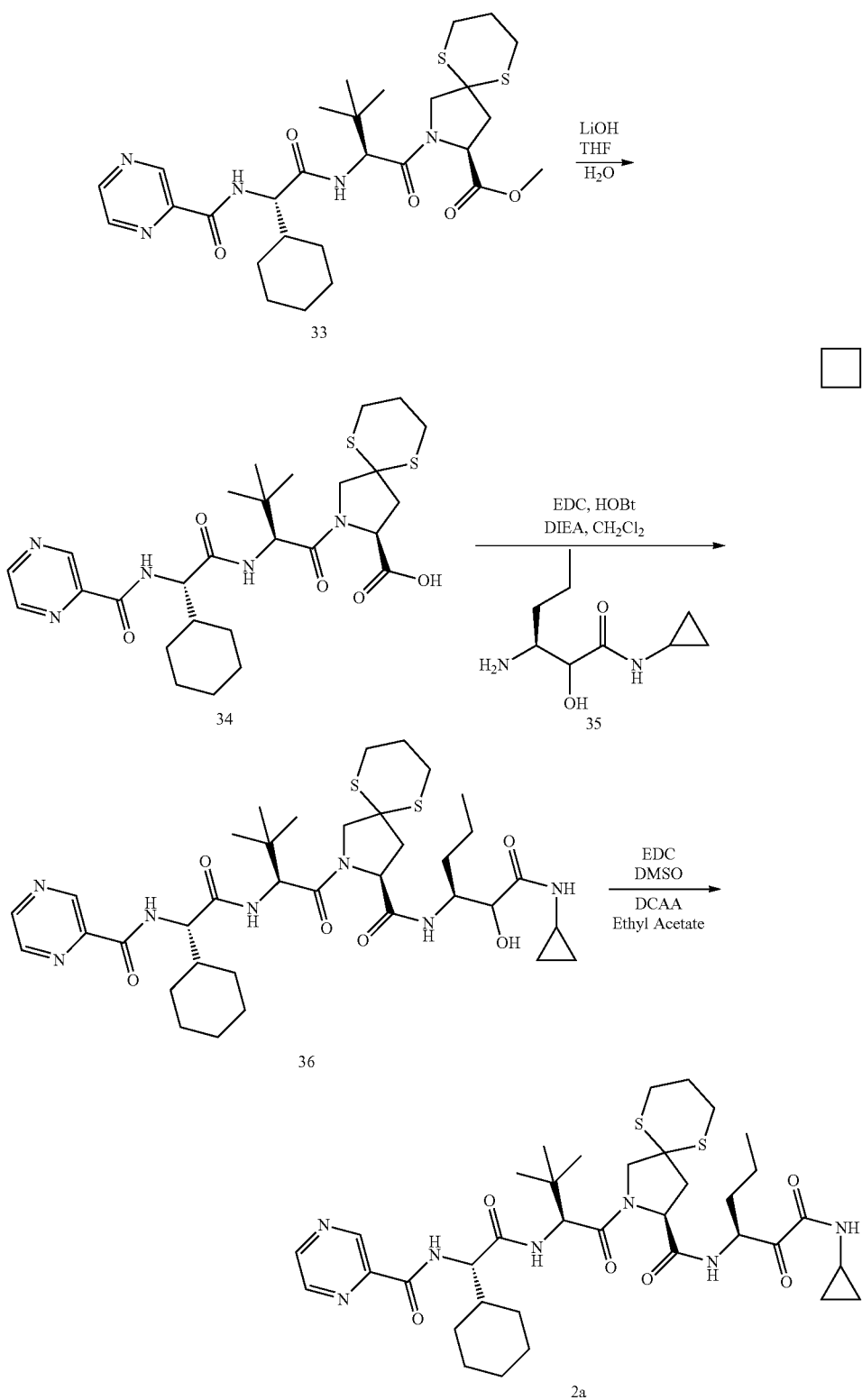
Scheme 5 above provides a synthetic route for the preparation of compound 2a. Compounds 3a, 5a, 6a, and 7a were also prepared generally according to scheme 5. One of skill in the art will also recognize that compounds of formula 2a, 3a, 5a, 6a, and 7a may also be prepared from intermediate 46 using the conditions described above in Scheme 1B.

Scheme 6:
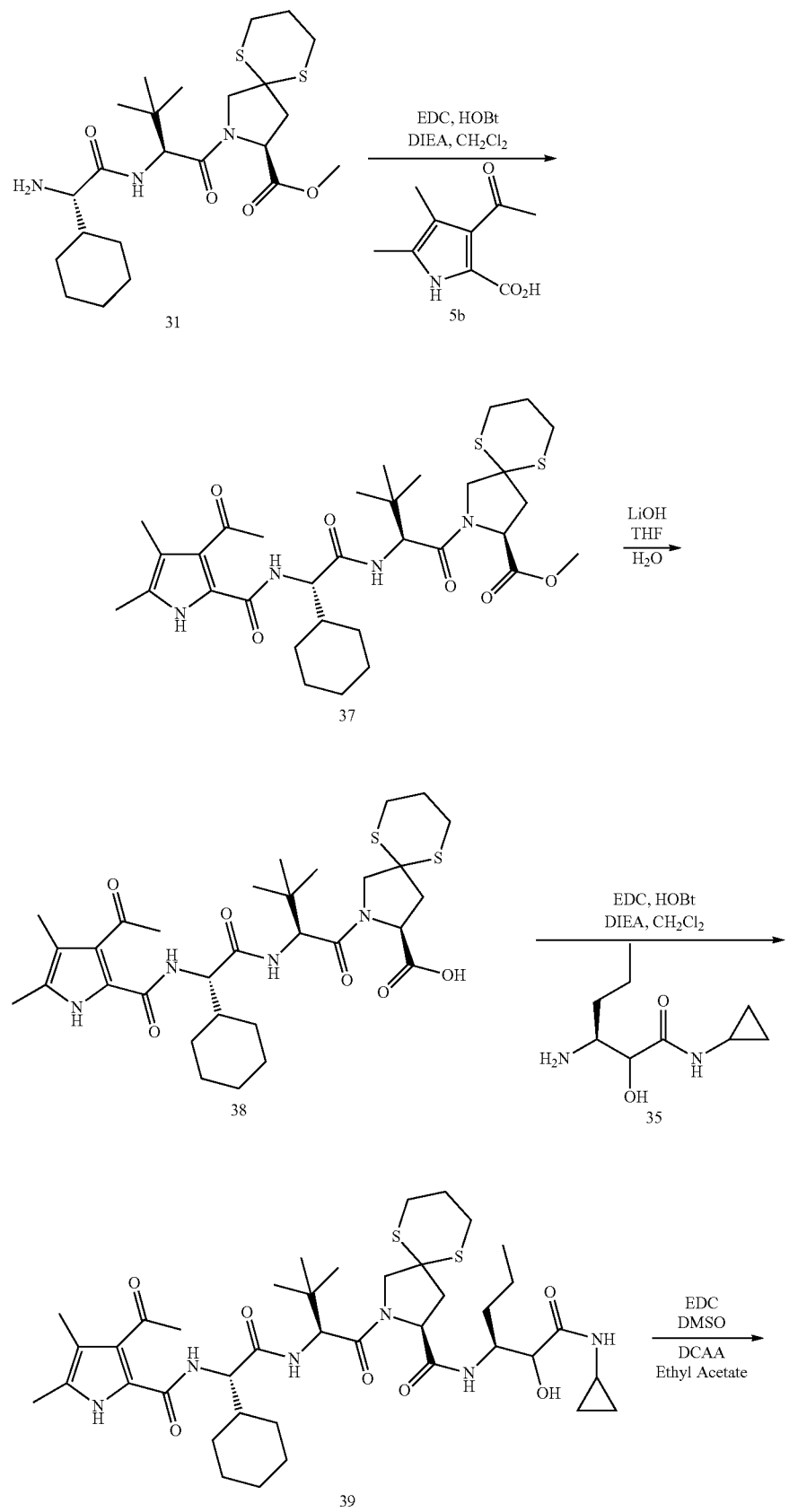

-continued

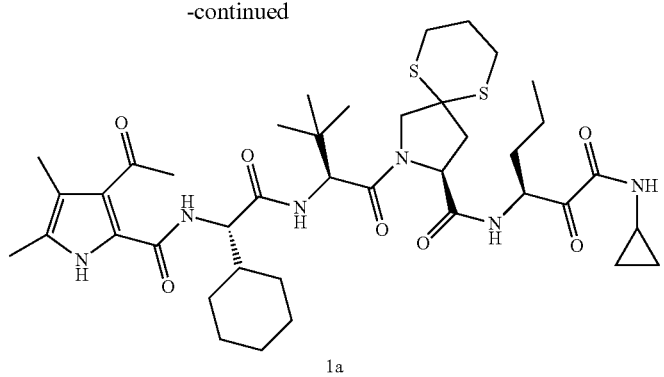

1a

Scheme 6 above provides a synthetic route for the preparation of compound 1a. Compound 4a was also prepared generally according to scheme 6. One of skill in the art will also recognize that compounds of formula 1a may also be prepared from intermediate 46 using the conditions described above in Scheme 1B.

Although certain exemplary embodiments are depicted and described below, it will be appreciated that compounds of this invention can be prepared according to the methods described generally above using appropriate starting materials generally available to one of ordinary skill in the art.

Another embodiment of this invention provides a pharmaceutical composition comprising a compound of formula I or formula Ia or a pharmaceutically acceptable salt thereof. According to one embodiment, the compound of formula I or formula Ia is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to one embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I or formula Ia and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In another embodiment, the pharmaceutical compositions are formulated for oral administration.

In one embodiment, the compositions of this invention additionally comprise another agent, such as a cytochrome P-450 inhibitor. Such cytochrome P-450 inhibitors include, but are not limited to, ritonavir.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. According to one embodiment, the CYP inhibitors include ritonavir, ketoconazole, troleandomycin, 4-methyl pyrazole, cyclosporin, and clomethiazole.

Methods for measuring the ability of a compound to inhibit cytochrome P50 monooxygenase activity are known (see U.S. Pat. No. 6,037,157 and Yun, et al. *Drug Metabolism & Disposition*, vol. 21, pp. 403-407 (1993).

A CYP inhibitor employed in this invention may be an inhibitor of only one isozyme or more than one isozyme. If the CYP inhibitor inhibits more isozyme, the inhibitor may nevertheless inhibit one isozyme more selectively than another isozyme. Any such CYP inhibitors may be used in a method of this invention.

In a method of this invention, the CYP inhibitor may be administered together with the Hepatitis C virus NS3/4A protease inhibitor in the same dosage form or in separate dosage forms.

If the CYP inhibitor and protease inhibitor are administered in separate dosage forms, each inhibitor may be administered about simultaneously. Alternatively, the CYP inhibitor may be administered in any time period around administration of the protease inhibitor. That is, the CYP inhibitor may be administered prior to, together with, or following the NS3/4A protease inhibitor. The time period of administration should be such that the CYP inhibitor affects the metabolism of the protease inhibitor. For example, if the protease inhibitor is administered first, the CYP inhibitor should be administered before the protease inhibitor is substantially metabolized and/or excreted (e.g., within the half-life of the protease inhibitor).

In another embodiment, the compositions of this invention additionally comprise another anti-viral agent, preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including metalloprotease, helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including metalloprotease, helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);

Gradient/Gradient Time: 10-90% CH$_3$CN/H2O over 9 minutes, then 100% CH$_3$CN for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

3-acetyl-4,5-dimethyl-2-pyrrole carboxylic acid (5b)

A solution of sodium nitrite (36.9 g, 0.534 mol) in 70 mL of water was added dropwise to a stirred solution of ethylacetoacetate (70 g, 0.538 mol) in 1401 mL of glacial acetic acid at 0° C. After the addition was complete, the light yellow reaction mixture was allowed to warm to room temperature. After 30 minutes, all the starting material had been consumed, the reaction was quenched with 350 mL of water and extracted with ethyl acetate (2×125 mL). The organic extracts were combined and washed with water (2×125 mL) and saturated sodium hydrogen carbonate aqueous solution (2×105 mL). The organic layer was dried with sodium sulfate and concentrated in vacuo to give 84.2 g (98%) of ethyl-2-Hydroxyimino-3-oxobutanoate 1b as a pale yellow oil. $^1$H NMR (CDCl$_3$) δ 10.3 (s, 1H), 4.2 (q, 2H), 2.3 (s, 3H), 1.3 (t, 3H) ppm.

Crushed sodium (12.4 g, 0.540 mol) was added to a solution of 2-butanone (48.2 mL, 0.538 mol) and ethyl formate (43.47 mL, 0.538 mol) in dry ether (540 mL) with vigorous mechanical stirring over a period of 1 h, during which time the mixture was chilled in an ice-salt bath. The mixture was then stirred at room temp. for 14 hours. After cooling the reaction mixture to 4° C. for a few hours, the precipitated sodium salt was obtained by filtration and washed thoroughly with cold, dry ether to afford 49.3 g (75%) of the desired sodium salt of 2-methy-3-oxobutyraldehyde 2b. $^1$H NMR (DMSO-d$_6$) δ 9.1 (s, 1H), 1.9 (s, 3H), 1.3 (s, 3H) ppm.

Sodium salt 2b (49.3 g, 0.404 mol) and oxime 1b (64.23, 0.404 mol) were stirred in 300 mL of 70% acetic acid/30% water and warmed to 50° C. Zinc powder (42.21 g, 0.646 mol) was added portion-wise over 30 minutes maintaining the temperature below 100° C. When the addition was complete, the suspension was refluxed for 15 minutes, then poured into 4 L of ice-water. After a short time, the product precipitated out to give, after filtration, 30.1 g (45%) of the desired ethyl-4,5-dimethyl-2-pyrrole carboxylate 3b. $^1$H NMR (CDCl$_3$) δ 9.0 (bs, 1H), 6.7 (s, 1H), 4.3 (q, 2H), 2.3 (s, 3H), 2.0 (s, 3H), 1.3 (t, 3H) ppm.

To a solution of aluminum chloride (50.19 g, 0.376 mol) in dry dichloroethane (580 mL) at 25° C. was added slowly acetic anhydride (17.75 mL, 0.188 mol). The resulting mixture was stirred at room temp. for 10 minutes, then a solution of pyrrole 3b (10.49 g, 0.0627 mol) in dichloroethane (30 mL) was added and the reaction mixture was stirred at room temp. for 2 hours. After an additional 3 hours at 80° C., the mixture was poured into ice water and extracted with dichloromethane. The organic layer was dried with anhydrous sodium sulfate and concentrated in vacuo to an orange residue. Short plug filtration over silica gel (30% ethyl acetate/70% hexanes) gave 7.5 g (60%) of ethyl-3-acetyl-4,5-dimethyl-2-pyrrole carboxylate 4b. $^1$H NMR (CDCl$_3$) δ 9.0 (bs, 1H), 4.3 (q, 2H), 2.7 (s, 3H), 2.1 (s, 3H), 1.9 (s, 3H), 1.3 (t, 3H) ppm.

A mixture of pyrrole ester 4b (8.2 g, 0.0392 mol), in ethanol and 100 mL of 10% potassium hydroxide were refluxed for 1 hour. The mixture was cooled and concentrated in vacuo to an oil. Water was added to the oil, the mixture acidified with dilute HCl and extracted with ether. The organic phase was dried with anh. sodium sulfate and concentrated in vacuo to a solid residue. The compound was recrystallized in 80 mL of ethanol to give 5.8 g of pure 3-acetyl-4,5-dimethyl-2-pyrrole carboxylic acid 5b as a solid. $^1$H NMR (DMSO-d$_6$) δ 2.5 (s, 3H), 2.2 (s, 3H), 2.0 (s, 3H) ppm.

Example 2

2-(2-{2-cyclohexyl-2-[(pyrazine-2-carbonyl)-amino]-acetylamino}-3,3-dimethyl-butyryl)-6,10-dithia-2-azaspiro[4.5]decane-3-carboxylic acid(1-cyclopropylaminooxalyl-butyl)-amide (2a)

To a solution of L-4-hydroxy-pyrrolidine-1,2-dicarboxylic acid 1-benzyl ester 2-methyl ester 1 (3.0 g, 1.0 eq, Advanced Chem Tech) in toluene (30 mL)/ethyl acetate (30 mL) was added NaBr (1.28 g, 1.14 eq) in water (5 mL). TEMPO (17 mg) was added, the mixture cooled to 4° C. and a solution of Clorox® (18 mL), sodium bicarbonate (2.75 g) and water (to 40 mL total volume) was added over 30 minutes. The resulting suspension was stirred 10 minutes before adding isopropanol (0.2 mL). The organic phase was separated and the aqueous phase extracted with ethyl acetate. The combined organic layers were washed with a 0.3 N solution of sodium thiosulfate and then brine, dried over sodium sulfate, filtered, and concentrated in vacuo to an amber oil. Purification via a silica gel plug eluting with an EtOAc/hexanes gradient (100% hexanes to 40% EtOAc/hexanes in 10% steps) afforded 2.85 g (96%) of 4-oxo-pyrrolidine-1,2-dicarboxylic acid 1-benzyl ester 2-methyl ester 2 as a clear oil. $^1$H NMR (CDCl$_3$) δ 7.35 (m, 5H), 5.15-5.30 (m, 2H), 4.80-4.90 (m, 1H), 3.95-4.05 (m, 2H), 3.80 (s, 3/5 of 3H), 3.65 (s, 2/5 of 3H), 3.0 (m, 1H), 2.65 (d, 3/5 of 1H), 2.60 (d, 2/5 of 1H) ppm.

Ketone 2 (250 mg) in CH$_2$Cl$_2$ at 15° C. was treated with 1,3-propanedithiol (100 uL) dropwise followed by BF$_3$OEt$_2$ (119 uL). The mixture was warmed to room temperature and stirred overnight. The reaction was quenched by adding 1 mL potassium carbonate aqueous solution (2 g/30 mL) followed by 321 uL of saturated sodium bicarbonate to adjust to pH 7-8. Washed organics with water, brine, then dried over anhydrous magnesium sulfate, filtered and concentrated in vacuo. Purification on a plug of silica gel eluting with toluene→hexane/ethyl ether (2:3→0:1) yielded 200 mg (60%) of desired 6,10-dithia-2-aza-spiro[4.5]decane-2,3-dicarboxylic acid-2-benzyl ester 3-methyl ester 26 as a clear oil. $^1$H NMR (CDCl$_3$) δ 7.30 (m, 5H), 5.05-5.25 (m, 2H), 4.6 (t, 0.5H), 4.55 (t, 0.5H), 3.8 (s, 1.5H), 3.75 (m, 1H), 3.6 (s, 1.5H), 2.95 (m, 1H), 2.85 (m, 3H), 2.75 (m, 1H), 2.4 (m, 0.5H), 2.35 (m, 0.5H), 2.0 (m, 2H) ppm.

Cbz-protected dithiane (50 mg) 26 in AcOH (140 uL) was treated with 30% HBr/AcOH (210 uL) and stirred for 2 hours at room temperature. Ethyl ether (20 mL) was added, the suspension stirred, solvent decanted off and then the procedure repeated twice more to give 40 mg (95%) of desired 6,10-dithia-2-aza-spiro[4.5]decane-3-carboxylic acid methyl ester 27 as a reddish-brown solid and as the HBr salt. $^1$H NMR (CDCl$_3$) δ 4.75 (t, 1H), 3.8 (s, 3H), 3.65 (d, 2H), 2.9-3.1 (m, 4H), 2.7 (m,1H), 2.55 (m, 1H), 1.95 (m, 1H), 1.85 (m, 1H) ppm.

L-Boc-tert-butyl glycine (243 mg, Bachem), EDC (201 mg), HOBt (161 mg), and DIEA (502 uL) in DMF (3 mL) was treated with the amine salt 27 (300 mg) in DMF (1 mL) and stirred at room temp. overnight. The mixture was partitioned between ethyl acetate and 1.0 N HCl, the organics washed with saturated sodium bicarbonate, 1.0 N glycine sodium salt solution, 10% potassium carbonate solution, and brine then dried over anhydrous sodium sulfate, filtered, and concentrated in vacuo. Purification on a plug of silica gel eluting with 30% EtOAc/hexanes afforded 300 mg (70%) of desired 2-(2-tert-butoxycarbonylamino-3,3-dimethyl-butyryl)-6,10-dithia-2-aza-spiro[4.5]decane-3-carboxylic acid methyl ester 28 as a white solid. $^1$H NMR (CDCl$_3$) δ 5.2 (d, 1H), 4.7 (t, 1H), 4.65 (s, 1H), 4.3 (d, 1H), 3.8 (d, 1H), 3.75 (s, 3H), 3.1 (m, 1H), 3.0 (m, 1H), 2.8 (m, 1H), 2.75 (m, 1H), 2.6 (m, 1H), 2.2 (m, 1H), 2.1 (m, 1H), 1.95 (m, 1H), 1.45 (s, 9H), 1.05 (s, 9H) ppm.

Boc protected amine 28 (243 mg) in dioxane (1 mL) was treated with a 4.0N HCl/dioxane solution (2 mL) and stirred for 2 hours at room temperature. The mixture was concentrated in vacuo, slurried in CH$_2$Cl$_2$ and evaporated in vacuo to give 208 mg (100%) of desired 2-(2-amino-3,3-dimethyl-butyryl)-6,10-dithia-2-aza-spiro[4.5]decane-3-carboxylic acid methyl ester 29 as a white solid and as the HCl salt. Mass Spec. MH+=347.1.

L-Boc-cyclohexyl glycine (154 mg, Bachem), EDC (115 mg), HOBt (81 mg), and DIEA (284 mg) in CH$_2$Cl$_2$ (1 mL) was treated with amine salt 29 (189 mg) in CH$_2$Cl$_2$ (2 mL) and the mixture stirred for 2 hours. The mixture was partitioned between ethyl acetate and 1.0 N HCl, the organics washed with sodium bicarbonate, 1.0 N glycine sodium salt solution, 10% potassium carbonate solution and brine then dried over sodium sulfate, filtered, and concentrated in vacuo. Purification on a plug of silica gel eluting with 30% EtOAc/hexanes afforded 221 mg (70%) of 2-[2-tert-butoxycarbonylamino-2-cyclohexyl-acetylamino)-3,3-dimethyl-butyryl]-6,10-dithia-2-aza-spiro[4.5]decane-3-carboxylic acid methyl ester 30 as a white solid.

$^1$H NMR (CDCl$_3$) δ 6.4 (d, 1H), 5.0 (d, 1H), 4.7 (m, 2H), 4.6 (d, 1H), 3.9 (m, 1H), 3.8 (d, 1H), 3.7 s, 1H), 3.0 (m, 2H), 2.8 (m, 1H), 2.7 (m, 1H), 2.6 (m, 1H), 2.2 (m, 1H), 2.15 (m, 1H), 2.0 (m, 1H), 1.65 (m, 7H), 1.45 (s, 9H), 1.15 (m, 4H), 1.05 (s, 9H) ppm.

Boc protected amine 30 (221 mg) in dioxane (1 mL) was treated with a 4.0N HCl/dioxane solution (2 mL) and stirred for 2 hours at room temperature. The mixture was concentrated in vacuo, slurried in CH$_2$Cl$_2$, evaporated, the procedure repeated and the mixture evaporated in vacuo to give 197 mg (100%) of desired 2-[2-(2-amino-2-cyclohexyl-acetylamino)-3,3-dimethyl-butyryl]-6,10-dithia-2-aza-spiro[4.5]decane-3-carboxylic acid methyl ester 31 as a white solid and as the HCl salt. Mass spec. MH+=486.2.

Pyrazine acid 32 (26 mg, Aldrich Chem Co.), EDC (40 mg), HOBt (32 mg), and DIEA (99 uL) in CH$_2$Cl$_2$ (2 mL) was treated with amine salt (98 mg) in CH$_2$Cl$_2$ (2 mL) and stirred at RT for 3 hours. The mixture was partitioned between EtOAc and 1.0N HCl washed with brine then dried over sodium sulfate, filtered, and concentrated in vacuo. Purification on a plug of silica gel eluting with 100% EtOAc afforded 50 mg (45%) of desired 2-[2-{2-cyclohexyl-2-[(pyrazine-2-carbonyl)-amino]-acetylamino}-3,3-dimethyl-butyryl)-6,10-dithia-2-aza-spiro[4.5]decane-3-carboxylic acid methyl ester 33 as a white solid. Mass spec. MH+=592.1, MH−=590.2.

Ester 33 (50 mg) in THF-water (400 uL-100 uL) was treated with LiOH (7 mg) and the mixture stirred for 3 hours at room temperature. The mixture was evaporated, diluted with EtOAc, washed with 1.0N HCl and brine then dried over magnesium sulfate, filtered, and concentrated in vacuo to give 2-[2-{2-cyclohexyl-2-[(pyrazine-2-carbonyl)-amino]-acetylamino}-3,3-dimethyl-butyryl)-6,10-dithia-2-aza-spiro[4.5] decane-3-carboxylic acid 34 as a white solid which was used in the next step without further purification. Mass Spec. MH+=578.0, MH−=576.2.

Acid 34 (49 mg), EDC (14.2 mg), HOBt (17.8 mg), and DIEA (44 uL) in CH$_2$Cl$_2$ (1 mL) was treated with 3-amino-2-hydroxy-hexanoic acid cyclopropylamine 35 (17.3 mg, prepared according to the methods described by U. Schoellkopf et al., *Justus Liebigs Ann. Chem.* GE, 1976, 183-202, and J. Stemple et al., *Organic Letters* 2000, 2(18), 2769-2772) in CH$_2$Cl$_2$ (1 mL) and the mixture stirred overnight at RT. EtOAc was added, the organics washed with 1.0N HCl and brine, then dried over sodium sulfate, filtered, and concentrated in vacuo. Purification on a plug of silica gel eluting with 2% MeOH/CH$_2$Cl$_2$ afforded 31 mg (50%) of desired 2-[2-{2-cyclohexyl-2-[(pyrazine-2-carbonyl)-amino]-acetylamino}-3,3-dimethyl-butyryl)-6,10-dithia-2-aza-spiro[4.5] decane-3-carboxylic acid[1-(cyclopropylaminooxalyl-butyl)-amide 36 as a white solid. Mass spec. MH+=746.1, MH−=744.3.

Hydroxyamide 36 (31 mg) in EtOAc (620 uL) was treated with EDC (120 mg) followed by DMSO (233 uL), then dichloroacetic acid (34 uL) and the mixture stirred for 30 minutes at room temp. The reaction mixture was diluted with 1.0N HCl (620 uL), the organics washed with water, then concentrated in vacuo and purified by preparative HPLC to give 14 mg (45%) of desired 2-(2-{2-cyclohexyl-2-[(pyrazine-2-carbonyl)-amino]-acetylamino}-3,3-dimethyl-butyryl)-6,10-dithia-2-aza-spiro[4.5]decane-3-carboxylic acid (1-cyclopropylaminooxalyl-butyl)-amide 2a as a white solid. $^1$H NMR (CDCl$_3$) δ 9.4 (s, 1H), 8.75 (s, 1H), 8.65 (s, 1H), 8.3 (s, 1H), 7.45 (d, 1H), 6.8 (d, 1H), 5.4 (d, 1H), 4.8 (m, 2H), 4.6 (m, 1H), 4.5 (m, 1H), 3.7 (d, 1H), 3.1 (m, 2H), 2.8 (m, 2H), 2.65 (m, 2H), 2.3 (m, 1H), 2.2 (m, 1H), 1.95 (m, 3H), 1.7 (m, 6H), 1.4 (m, 2H), 1.15 (m, 4H), 1.05 (s, 9H), 0.9 (m, 4H), 0.85 (m, 2H), 0.65 (m, 2H) ppm.

Example 3

2-(2-{2-[(3-acetyl-4,5-dimethyl-1H-pyrrole-2-carbonyl)-amino]-2-cyclohexyl-acetylamino}-3,3-dimethyl-butyryl)-6,10-dithia-2-aza-spiro[4.5]decane-3-carboxylic acid(1-cyclopropylaminooxalyl-butyl)-amide (1a)

This compound was prepared from 2-[2-(2-amino-2-cyclohexyl-acetylamino)-3,3-dimethyl-butyryl]-6,10-dithia-2-aza-spiro[4.5]decane-3-carboxylic acid methyl ester 31 (prepared as described above in example 2) and 3-acetyl-4,5-dimethyl-2-pyrrole carboxylic acid 5b (prepared as described above in example 1) using procedures similar to those described in example 2. The title compound was isolated as a white solid (11% for last step). LCMS: retention time=4.8 min, M+H=801.2.

Example 4

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit.

10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

Example 5

HCV Ki Assay Protocol

HPLC Microbore Method for Separation of 5AB Substrate and Products
Substrate:
NH$_2$-Glu-Asp-Val-Val-(alpha)Abu-Cys-Ser-Met-Ser-Tyr-COOH A stock solution of 20 mM 5 AB (or concentration of your choice) was made in DMSO w/0.2M DTT. This was stored in aliquots at −20 C.

Buffer: 50 mM HEPES, pH 7.8; 20% glycerol; 100 mM NaCl

Total assay volume was 100 μL

|  | X1 (μL) | conc. in assay |
|---|---|---|
| Buffer | 86.5 | see above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5 AB).

Incubated for 20 min at 30 C.

Terminated reaction by addition of 25 μL of 10% TFA

Transferred 120 μL aliquots to HPLC vials

Separated SMSY product from substrate and KK4A by the following method:

Microbore Separation Method:

Instrumentation: Agilent 1100

Degasser G1322A

Binary pump G1312A

Autosampler G1313A

Column thermostated chamber G1316A

Diode array detector G1315A

Column:

Phenomenex Jupiter; 5 micron C18; 300 angstroms; 150×2 mm; P/O 00F-4053-B0

Column thermostat: 40 C

Injection volume: 100 μL

Solvent A=HPLC grade water+0.1% TFA

Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min

Post-run time: 10 min.

Table 1 below depicts Mass Spec. (M−H, M+H, obs=observed), HPLC, $^1$H-NMR ("Yes" if spectral data obtained), Ki, and IC$_{50}$ data for certain compounds of the invention.

Compounds with Ki's ranging from 1 μM to 5 μM are designated A. Compounds with Ki's ranging from 1 μM to 0.5 μM are designated B. Compounds with Ki's below 0.5 μM are designated C. Compounds with IC$_{50}$'s ranging from 1 μM to 5 μM are designated A. Compounds with IC$_{50}$'s ranging from 1 μM to 0.5 μM are designated B. Compounds with IC$_{50}$'s below 0.5 μM are designated C.

TABLE 1
| Compound | MS+ (obs) | MS− (obs) | HPLC, R$_t$(min) | Ki | IC$_{50}$ | $^1$H-NMR (CDCl$_3$) |
|---|---|---|---|---|---|---|
| 1a | 801.2 | 799.2 | 4.80 | C | C | Yes |
| 2a | 744.0 | 742.2 | 4.0 | C | C | Yes |
| 3a | 704.4 | 702.6 | 3.63 | C | C | Yes |
| 4a | 761.1 | 759.3 | 3.77 | C | C | Yes |
| 5a | 744.2 | 742.1 | 4.05 | C | — | Yes |
| 6a | 744.2 | 742.3 | 3.94 | C | — | Yes |
| 7a | 730.2 | 728.3 | 3.90 | C | C | Yes |
All of the documents cited herein, are incorporated herein by reference.
We claim:
1. A compound selected from the group comprising:
1a
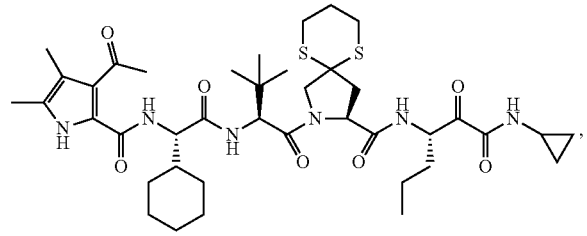
3a
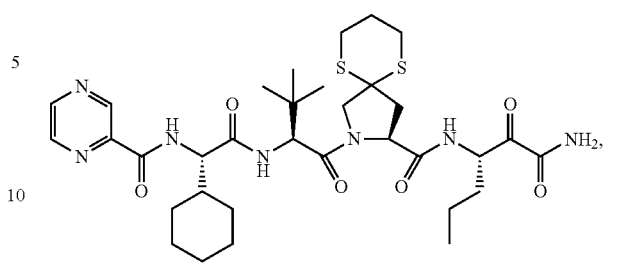
4a
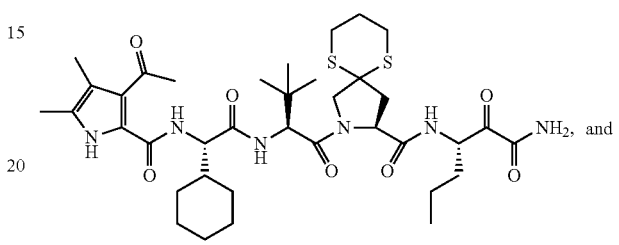
, and
7a
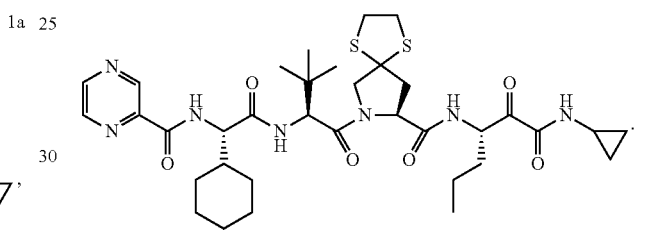
.
* * * * *